United States Patent
Jain et al.

(10) Patent No.: US 12,334,323 B2
(45) Date of Patent: Jun. 17, 2025

(54) DYNAMIC PROCESSING OF MASS SPECTROMETRY SIGNALS WHILE ADJUSTING FOR COMPUTING STORAGE AND PROCESSING RESTRICTIONS

(71) Applicant: Sapient Bioanalytics, LLC, San Diego, CA (US)

(72) Inventors: Mohit Jain, San Diego, CA (US); Saumya Tiwari, San Diego, CA (US); Jeramie Watrous, San Diego, CA (US)

(73) Assignee: Sapient Bioanalytics, LLC, San Diego, CA (US)

( * ) Notice: Subject to any disclaimer, the term of this patent is extended or adjusted under 35 U.S.C. 154(b) by 476 days.

(21) Appl. No.: 17/750,249

(22) Filed: May 20, 2022

(65) Prior Publication Data

US 2023/0377861 A1 Nov. 23, 2023

(51) Int. Cl.
| | |
|---|---|
| H01J 49/00 | (2006.01) |
| G01N 30/72 | (2006.01) |
| G01N 30/86 | (2006.01) |
| G01N 30/02 | (2006.01) |

(52) U.S. Cl.
CPC ...... *H01J 49/0036* (2013.01); *G01N 30/7233* (2013.01); *G01N 30/8624* (2013.01); *G01N 2030/027* (2013.01)

(58) Field of Classification Search
CPC ............. G01N 2030/027; G01N 30/72; G01N 30/7233; G01N 30/86; G01N 30/8624; G16C 20/70; G16C 20/90; H01J 49/0036
See application file for complete search history.

(56) References Cited

U.S. PATENT DOCUMENTS

| | | | | |
|---|---|---|---|---|
| 7,359,805 B1* | 4/2008 | Cetto | ................. | H01J 49/0036 436/171 |
| 2005/0066227 A1* | 3/2005 | Chia | ................. | G06F 12/0893 711/170 |
| 2007/0005254 A1* | 1/2007 | Nilsson | ............. | G01N 30/8651 702/19 |
| 2008/0306898 A1* | 12/2008 | Tsypin | ............... | G06F 18/2414 706/61 |
| 2009/0001262 A1* | 1/2009 | Visser | ............... | G06F 18/21342 250/281 |
| 2010/0061605 A1* | 3/2010 | Fain | ...................... | G06T 7/0012 382/128 |
| 2014/0380015 A1* | 12/2014 | Lasser | .................. | G06F 12/023 711/170 |

(Continued)

OTHER PUBLICATIONS

Race et al., Memory Efficient Principal Component Analysis for the Dimensionality Reduction of Large Mass Spectrometry Imaging Data Sets, Anal. Chem. 85, 2013 (Year: 2013).*

(Continued)

*Primary Examiner* — Kyle R Quigley
(74) *Attorney, Agent, or Firm* — Sheppard Mullin Richter & Hampton LLP

(57) ABSTRACT

Systems and methods are provided for obtaining raw mass spectrometry data from samples, extracting a subset of the raw mass spectrometry data based on storage characteristics of the computing system, storing the subset of the raw mass spectrometry data within a storage of the computing system, and transmitting the stored subset to a machine learning component.

12 Claims, 30 Drawing Sheets

(56) References Cited

U.S. PATENT DOCUMENTS

| | | | |
|---|---|---|---|
| 2015/0123825 A1* | 5/2015 | De Corral | H03M 7/3059 |
| | | | 250/282 |
| 2017/0074826 A1* | 3/2017 | Clowers | H01J 49/0036 |
| 2019/0378702 A1* | 12/2019 | Athanas | H01J 49/0004 |
| 2022/0310374 A1* | 9/2022 | Lam | H01J 49/027 |

OTHER PUBLICATIONS

Palmer et al., The Use of Random Projections for the Analysis of Mass Spectrometry Imaging Data, J. Am. Soc. Mass Spectrom., 2015 (Year: 2015).*

Thomas et al., Dimensionality Reduction of Mass Spectrometry Imaging Data using Autoencoders, IEEE, 2016 (Year: 2016).*

Thomas et al., Enhancing Classification of Mass Spectrometry Imaging Data with Deep Neural Networks, IEEE, 2017 (Year: 2017).*

Lieb et al., Peak detection for MALDI mass spectrometry imaging data using sparse frame multipliers, arXiv, 2019 (Year: 2019).*

* cited by examiner

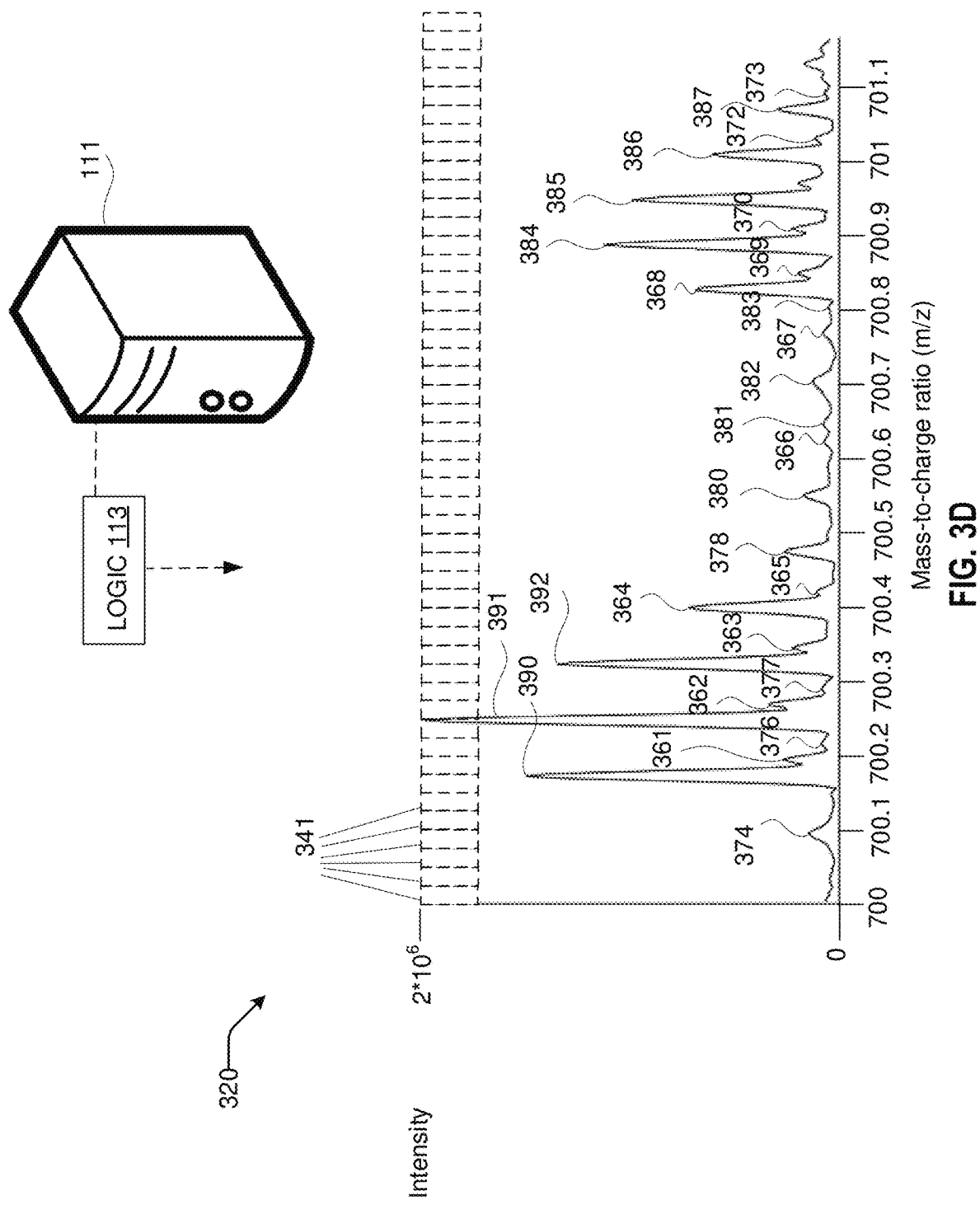

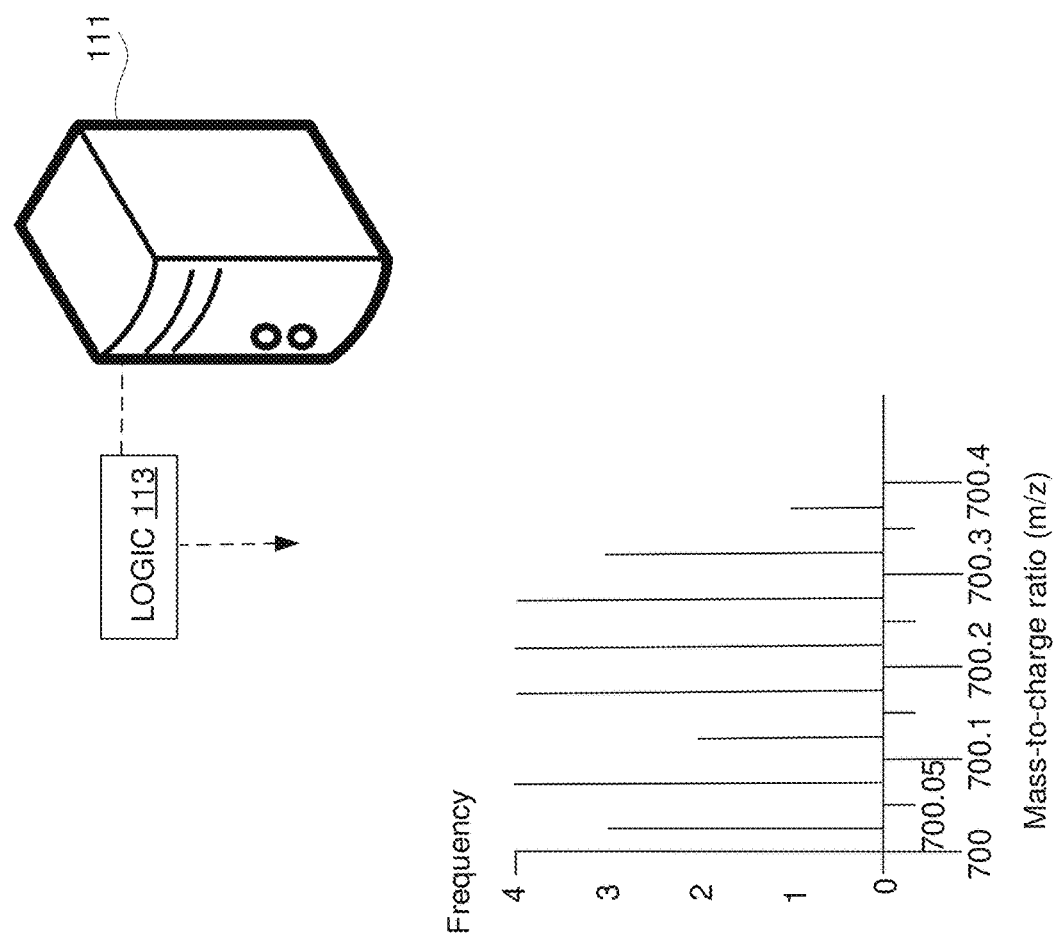

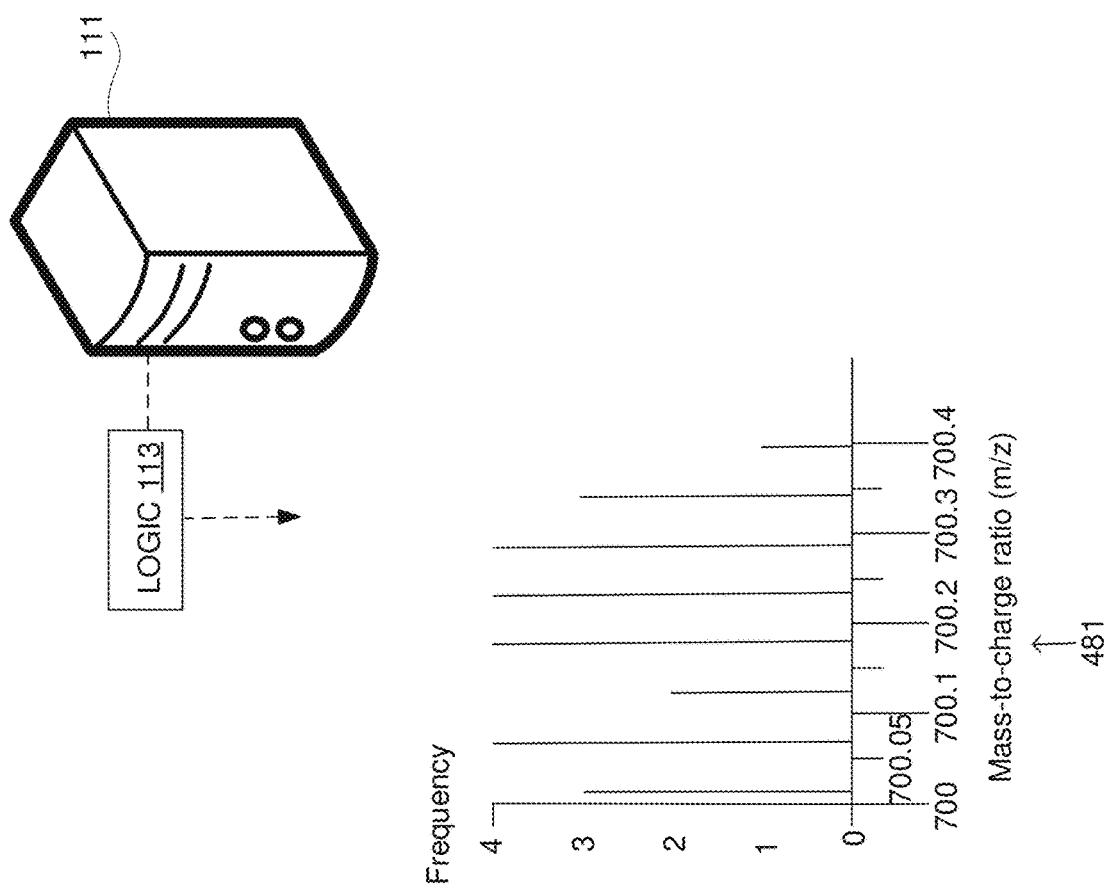

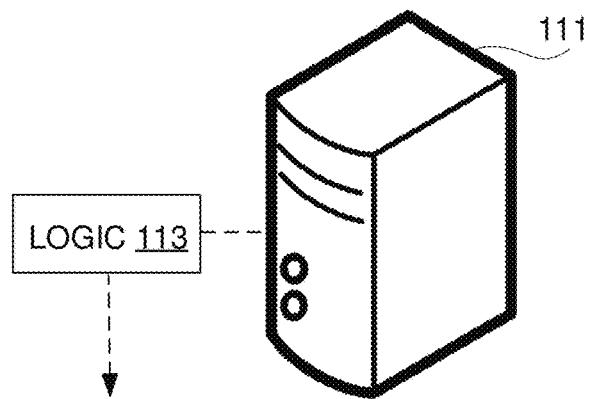
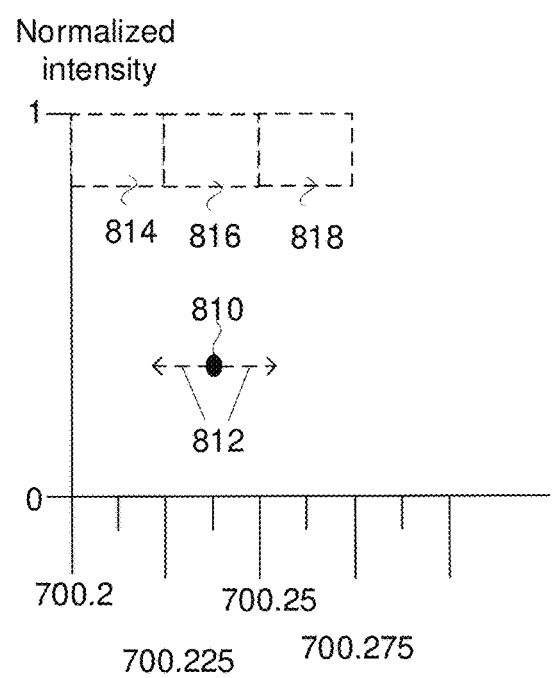
FIG. 8

DYNAMIC PROCESSING OF MASS SPECTROMETRY SIGNALS WHILE ADJUSTING FOR COMPUTING STORAGE AND PROCESSING RESTRICTIONS

BACKGROUND

Mass spectrometry separates a solid, liquid, or gaseous sample into individual constituents based on the mass-to-charge ratio of the constituents. Such separation elucidates the composition of a complex sample. Mass spectrometry entails bombarding the sample with an ion source such as an electron beam, which causes the sample to break up into constituents that become positively charged ions. Subsequently, a mass analyzer may separate these constituents according to their mass-to-charge ratios. For example, an electric or magnetic field may be applied to the constituents while the constituents are accelerated. The mass-to-charge ratios may be measured based on amounts of deflection of the constituents. A detector such as an electron multiplier may detect intensities of the constituents at each of different mass-to-charge ratios. A spectrum of intensity as a function of mass-to-charge ratios illustrates intensities, representing amounts of the constituents of the sample, at each of the mass-to-charge ratios. Therefore, mass spectrometry identifies, quantifies, and characterizes the individual constituents of a sample.

However, implementation of mass spectrometry for analysis of complex biological samples may require coupling to additional chemical approaches for further separating biological components prior to introduction into a mass spectrometer. For example, mass spectrometry may be augmented with upstream chromatography processes, in particular, liquid chromatography (high performance liquid chromatography [HPLC]), that separates a sample, such as bodily fluids, based on chemical properties. Samples may be inputted or injected into a liquid chromatography column, which includes a stationary phase bonded or adsorbed to a surface of the column. Due to differences in binding to the column of individual compounds, molecules, or chemicals with the sample, the individual compounds, molecules, or chemicals are retained within the column for different durations. Thus, liquid chromatography separates the individual compounds, molecules, or chemicals based on their retention times to the column, prior to introduction into a mass spectrometer. An extracted ion chromatogram from a mass spectrometer illustrates intensities, representing amounts of the individual compounds, molecules, or chemicals, sharing the same mass to charge ratio at different retention times. By selecting a particular mass-to-charge ratio, individual compounds, molecules, or chemicals may be separated due to their different retention times.

BRIEF DESCRIPTION OF THE DRAWINGS

The present disclosure, in accordance with one or more various examples, is described in detail with reference to the following figures. The figures are provided for purposes of illustration only and merely depict typical examples.

FIGS. 3C-3E are exemplary illustrations of a computing component that applies different bin values in a mass spectrum.

FIGS. 4A-4C are exemplary illustrations of a computing component that applies different bin values in a mass spectrum, while illustrating a concept of determining frequencies of occurrence of signals across all data samples.

FIGS. 6A-6D illustrate expansion of windows when no conflicts exist between neighboring windows. FIGS. 6E-6F illustrate expansion of windows when a conflict exists between neighboring windows.

FIG. 8 is an exemplary illustration of a computing component that expands a window along a mass-to-charge ratio axis.

Figure 1:
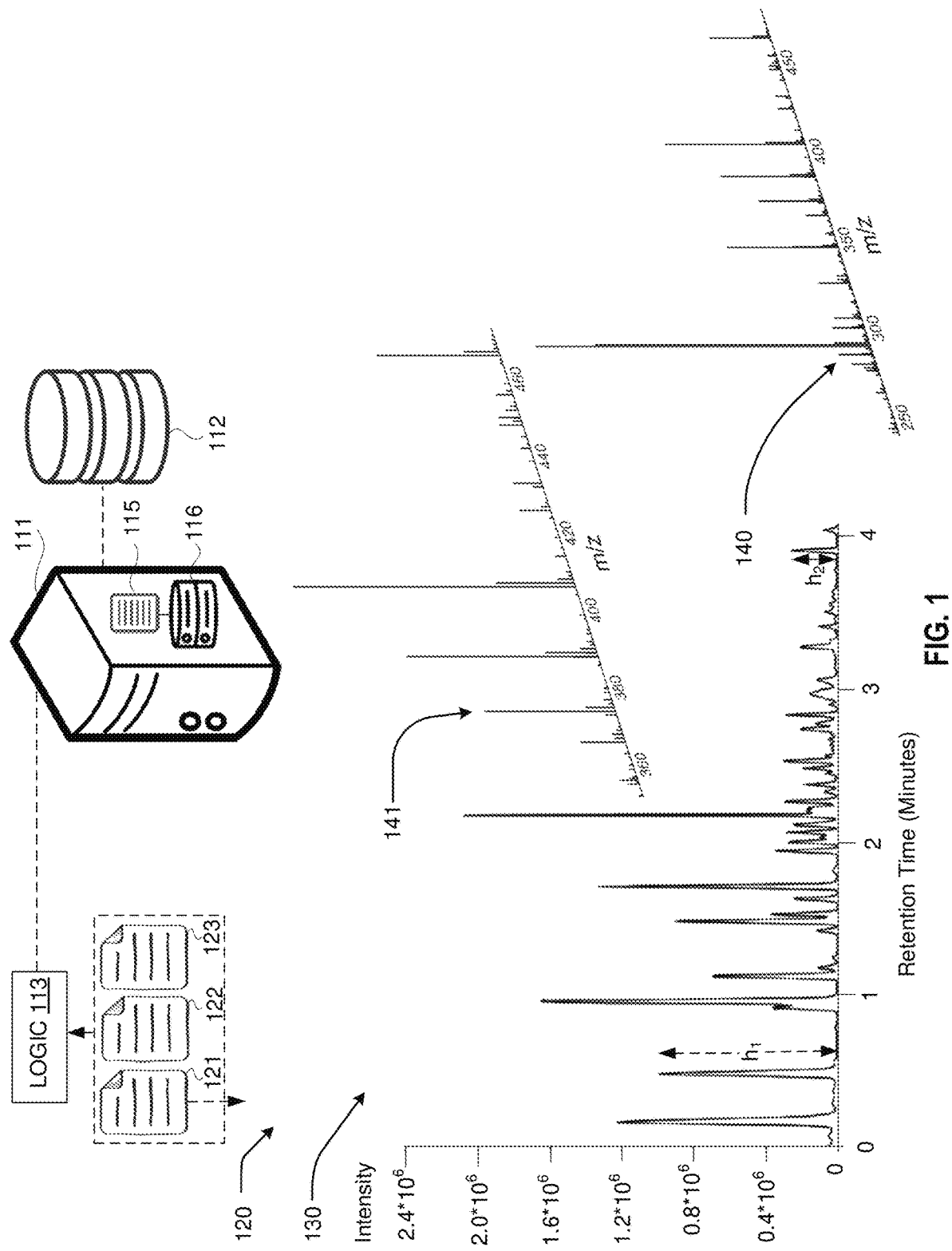
FIG. 1 is an exemplary illustration of a computing system that receives raw data from a mass spectrometer, processes, reformats, and/or transforms the raw data in preparation for analysis and other operations by a machine learning model.

The figures are not exhaustive and do not limit the present disclosure to the precise form disclosed.

DETAILED DESCRIPTION

Mass spectrometry, especially when paired with chromatography, has provided a cornucopia of benefits in identification, quantification, and characterization of samples. mass spectrometry may include limitations such as minor errors in measured mass to charge ratios, prevalence of noise, and occasional failure to detect actual signals of compounds, molecules, or chemicals. Therefore, some actual compounds, molecules, or chemicals present in a sample may be undetected or difficult to distinguish from noise signals. Moreover, false positives may be included in the raw data from mass spectrometry. Data extraction and processing approaches have not only failed to adequately address such shortcomings, but have also yielded inconsistent results. These limitations are further exacerbated by ever-increasing demands of processing Gargantuan quantities of data, generally at least on a scale of thousands of samples. Generally, the data extraction and processing approaches are ill-equipped to handle such a scale of samples. Moreover, manual processing is infeasible on an order of thousands of samples. Thus, conventional mass spectrometry data extraction techniques are plagued by inefficiency and unreliability.

Examples described herein address these challenges by implementing an image-based processing approach, rather than a signal-based approach. In particular, a computing component that receives raw data from a mass spectrometer, processes, reformats and/or transforms the raw data, and feeds or inputs the transformed data into a machine learning component or model that is separate from the computing component, or implements a machine learning model that is associated with or within the computing component to analyze the transformed data. Following the implementation of the machine learning model, the computing component, or a separate computing component, may receive the output from the machine learning model. Based on the output, the computing component, or the separate computing component, may perform additional analysis, processing, and/or other functions. For example, the output may include predictions and/or information indicating readings or values of retention time and/or mass to charge ratio across a multitude of samples, along with probabilities of accuracy of such readings or values, or confidence intervals. From such information, the computing component may derive, infer, or determine an elemental or isotopic signature of the sample, and chemical identities or structures of molecules or compounds within the sample. The computing component may, based on such information, perform diagnosis or treatment. In a particular example, if mass spectrometry were performed on blood samples from patients having particular symptoms, raw data from mass spectrometry may be processed and/or transformed by the computing component, then fed into a machine learning model which may output the constituents of the blood sample. From the constituents of the blood sample, the computing component may determine or detect that certain constituents are higher or lower compared to respective levels in non-symptomatic patients or subjects. Thus, the computing component may diagnose one or more particular disease conditions in the symptomatic patients, and/or develop or implement a treatment to restore the levels of the constituents back to normal ranges.

The examples described herein increases the accuracy of processed mass spectrometry data, by mitigating or eliminating the effects of noise and retaining signals that represent actual constituents of a sample. Additionally, the examples are tailored for a large scale of samples, such as a scale of thousands of samples, thereby attaining both accuracy and efficiency. Therefore, timing and consumption of resources, such as computing resources, are conserved. The examples described herein thus improve the functionality of a computer that carries out processing of mass spectrometry data faster and more accurately, while expediting and increasing reliability and efficacy of further downstream applications such as diagnoses, therapeutics, and prognoses, ultimately resulting in improved quality of life.

FIG. 1 is an exemplary illustration of computing system 110 including a computing component 111. The computing component 111 may include one or more hardware processors (e.g., central processing units (CPUs)) and logic 113 that implements instructions to carry out the functions of the computing component 111, which include, for example, receiving raw data from a mass spectrometer, processing, reformatting, and/or transforming the raw data, and feeding or inputting the transformed data into a machine learning component or model.

The computing component 111 may include one or more physical devices or servers, or cloud servers on which services or microservices run. The computing component 111 may store, in a database 112, raw mass spectrometry data from different samples, and/or reformatted, processed, or transformed mass spectrometry data. In some examples, the computing component 111 may store, at least temporarily, discarded portions of the raw mass spectrometry data, such as portions of the image representation that has been removed or filtered out, as will be illustrated, for example, in FIG. 5B. The database 112 may further store any results generated from the raw mass spectrometry data, such as absolute or relative intensities of signals, or amounts, of individual constituents, and/or respective mass-to-charge ratios and retention times of the constituents. The database 112 may be indexed by an index 115 to categorize or classify the information stored in the database 112. In some examples, the computing component 111 may cache at least a portion of the information stored in the database 112 in a cache 116, which may be part of an internal memory structure within the computing component 111. For example, the computing component 111 may cache any of the data within the database 112 that may be frequently accessed, referenced, or analyzed. For example, if a particular sample is part of different analyses, then information of that sample may be stored in the cache 116.

In particular, the computing component 111 may receive raw mass spectrometry data samples 121, 122, and 123, which may be in a data format of a text file and may be converted from a different data format as received from a mass spectrometer. The different data format, in some examples, may be in an eXtensible Markup Language. The different data format may be base-64 encoded and/or interleaved, and represented as a series of retention time, mass-to-charge ratio, and intensity tuples. Although only three raw mass spectrometry data samples for simplicity, FIG. 1 is not to be construed to mean or imply that the computing component 111 only receives a certain number of raw mass spectrometry data samples at one time instance. The computing component 111 may process any number of raw mass spectrometry data samples, such as on an order of at least a threshold number of samples (e.g., at least thousands of raw mass spectrometry data samples). Any or each of the raw mass spectrometry data samples 121, 122, and 123 may be manifested or stored as a tabular representation. However, FIG. 1 illustrates the raw mass spectrometry data samples 121, 122, and 123 as a pictorial representation 120 (e.g., a spectral representation), to more clearly illustrate the information that may be encompassed by the raw mass spectrometry data samples 121, 122, and 123. The pictorial representation 120 illustrates that the raw mass spectrometry data samples 121, 122, and 123 may include first data 130 generated by liquid chromatography regarding retention time of individual components (e.g., individual compounds, molecules, or chemicals) within the sample, on a first axis, and second data 140 and 141, corresponding to different retention times, generated by mass spectrometry regarding mass-to-charge ratios of individual constituents within the sample, on a second axis. For example, the first data 130 may include a total ion chromatogram or a base peak chromatogram. Meanwhile, the second data 140 and 141 may include mass spectrograms that indicate mass-to-charge ratios at specific retention times. For example, the second data 140 may correspond to a specific retention time of around 3.9 minutes, at which a local peak is located. The second data 141 may correspond to a specific retention time of around 2.2 minutes, at which another local peak is located.

In some examples, the first axis and the second axis may be orthogonal. Heights or amplitudes in a $h_1$ direction indicate respective intensities of signals, and/or respective amounts of individual components that correspond to specific retention times. Meanwhile, heights or amplitudes in a $h_2$ direction indicate respective intensities of signals, and/or respective amounts of individual constituents that correspond to specific mass-to-charge ratios.

Figure 2:
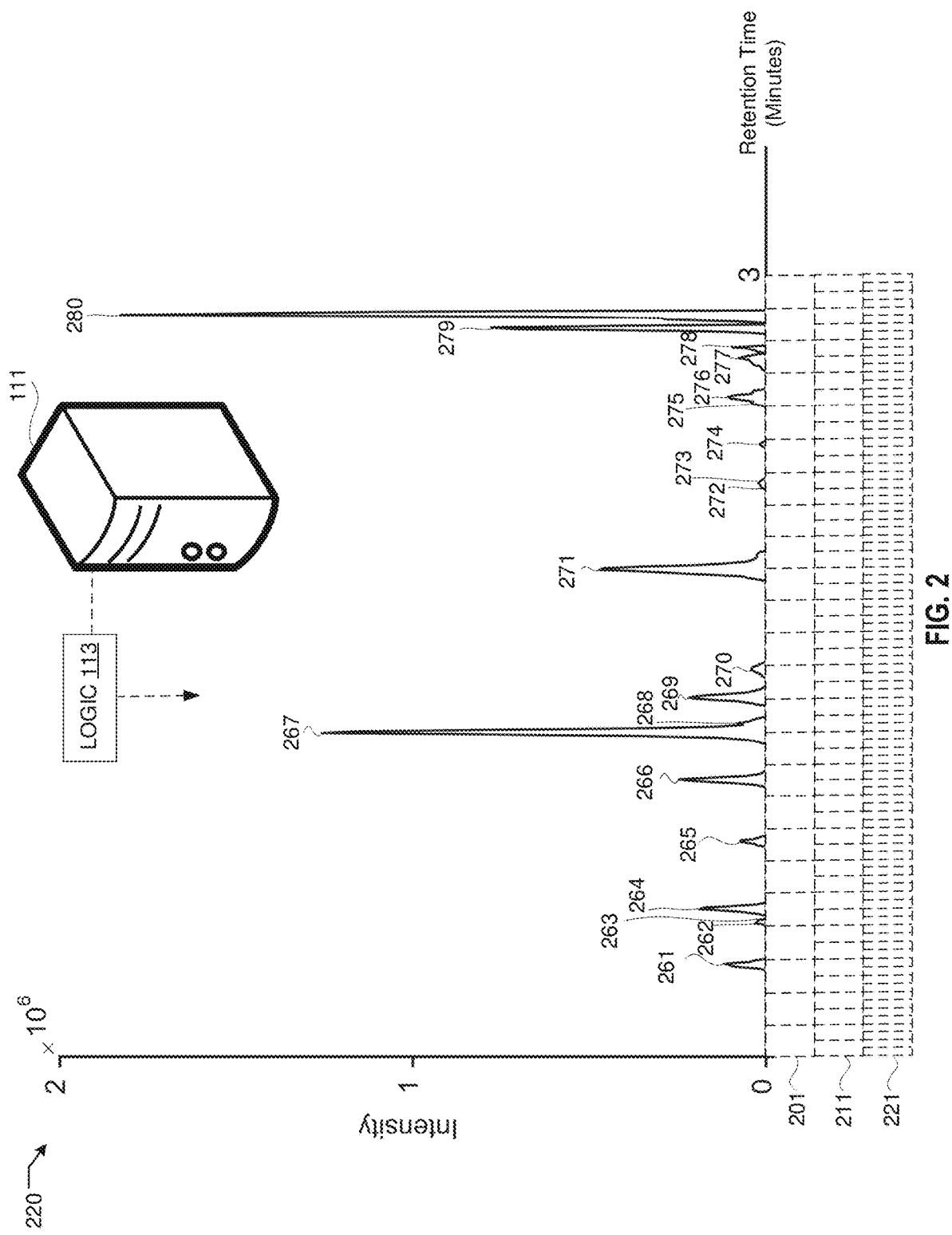
FIG. 2 is an exemplary illustration of a computing component that determines bin values and applies bin values on an extracted ion chromatogram, in a retention time dimension or axis.

Following the receipt of the multiple raw mass spectrometry data samples (hereinafter "data samples") 121, 122, and/or 123, the computing component 111 may process the multiple data samples. The processing may entail binning, or determining a bin value, in both a retention time axis, as illustrated in FIG. 2, and in a mass-to-charge ratio axis, as illustrated in FIGS. 3A-3E and 4A-4C. FIG. 2 illustrates an extracted ion chromatogram 220, corresponding to a single data sample. The extracted ion chromatogram 220 includes intensities of signals 261-280 as a function of retention time, at a specific mass-to-charge ratio or a specific range of mass-to-charge ratios.

Such a procedure of binning may first encompass determining local maxima over different intervals, or bins, of the retention time axis, as illustrated in FIG. 2, and the mass-to-charge ratio axis, as illustrated in FIGS. 3A-3E, at each data sample (e.g., the raw mass spectrometry data sample 121, the raw mass spectrometry data sample 122, the raw mass spectrometry data sample 123, and other data samples). As will be elaborated on subsequently, the local maxima may refer to the highest intensity signal in each interval or bin. In particular, the application of binning may encompass setting or determining a bin value or bin interval (hereinafter "bin value"). A bin value may refer to a particular interval length in which different signals within a particular bin are consolidated or merged into a single signal. Thus, within a single bin, signals originally captured or detected as distinct signals are no longer distinguished, and the computing component 111 may detect only a single signal having a maximum intensity within each bin. For example, referring to FIG. 2, if the computing component 111 determined the bin value in the retention time axis to be 0.125 minutes, then the computing component 111 would detect only a single signal, within a retention time between 0 and 0.125 minutes, a single signal within a retention time between 0.125 minutes and 0.25 minutes, a single signal within a retention time between 0.25 minutes and 0.375 minutes, and so on.

Increasing a bin value may reduce an amount of data to be processed, thereby decreasing a consumption of time and computing resources. However, a tradeoff of increasing the bin value may be a compromise in an amount of signals captured, or loss of signals. Therefore, the computing component 111 may determine a bin value that addresses both considerations. Generally, the determination of the bin value may be based on an amount of resources, with respect to time and/or computing resources, consumed in processing the data samples, and an amount of signals that would be lost or failed to be processed as a result of applying a particular bin value. In particular, the computing component 111 may determine a number of signals captured across all data samples at different bin values. More specifically, the computing component 111 may determine a bin value such that by increasing the bin value by a particular factor or a particular amount, no signals, or no more than a threshold number or proportion of signals, would be lost or failed to be captured as a result. This principle of determining a bin value may apply along both a retention time axis and a mass-to-charge ratio axis.

Thus, the computing component 111 may determine a bin value based on an amount or proportion of signals that would be lost or failed to be captured as a result of increasing the bin value. The increase in the bin value may be by discrete factors, for example, by a particular factor such as 2, 5, or 10. In such a manner, the computing component 111 may determine at which bin value the signal loss starts to become unacceptable (e.g., exceed a threshold proportion or threshold amount) upon increasing the bin value by the particular factor. Additionally or alternatively, the computing component 111 may determine a bin value based on an amount or proportion of signals that would be lost or failed to be captured compared to some given bin value.

In one example, the computing component 111 may set an initial bin value. According to the initial bin value, the computing component 111 may determine a number of captured signals across all the data samples. The computing component 111 may iteratively increase the initial bin value by a factor, and determine, at each iteration, whether an amount of captured signals decreases by more than a threshold proportion compared to a previous iteration. The computing component 111 may determine a particular bin value at which the amount of captured signals decreases by more than a threshold proportion upon increasing the particular bin value by the factor; and determine the particular bin value as the bin value to be applied. In other examples, the computing component 111 may iteratively decrease the initial bin value by a factor, and determine, at each iteration, an increase in an amount of captured signals, if the initial bin value results in an excessive signal loss.

In particular, the computing component 111 may determine a first total amount of signals captured at the first bin value. In some nonlimiting examples, the first bin value may be 0.01, 0.001, 0.0125, 0.125, 0.03125, or 0.0625 minutes. If the bin value is 0.125 minutes, then bins 201 having that bin value would be applied. The computing component 111 may further determine a second total number of signals captured at a second bin value, increased or decreased by a factor (e.g., 2, 5, or 10) compared to the particular bin value. For example, the second bin value may be 0.0625 minutes, using bins 211 having that size. If a difference, in number or in proportion, between the second total number of signals and the first total number of signals, or between the second total number of signals and an original total number of signals, is within a threshold, then the amount of signal loss that resulted by increasing the bin value to the second bin value from the first bin value may still be acceptable. In some nonlimiting examples, the threshold may be 1% or 5% with respect to an increase or decrease in the bin value by a factor of two. Then the computing component 111 may determine a third total number signals captured using a third bin value, such as 0.03125 minutes. The computing component 111 may continue to determine an amount of incremental or overall signal loss that resulted by increasing the bin value by a specific factor (e.g., a factor of two). Such a determination may be based on a total amount of signals captured at two consecutive bin values that differ by a factor, or a comparison between a total number of signals at the third bin value and at the first bin value. Once the amount of signal loss exceeds the threshold, then the computing component 111 may determine not to, or refrain from, increasing the bin value to the other bin value. For example, assume that the computing component 111 captured 1000 signals at a bin value of 0.0125 minutes and 970 signals at a bin value of 0.025 minutes, meaning that the signal loss was three percent. However, upon increasing the bin value to 0.05 minutes, the computing component 111 may have captured only 920 signals. The difference between the number of captured signals between the bin values of 0.0125 minutes and 0.05 minutes is eight percent, while the difference between the number of captured signals between the bin values of 0.025 minutes and 0.05 minutes is also over five percent. Thus, no matter what criteria is used to determine the difference of captured signals, the difference would exceed the threshold proportion. The computing component 111 may determine that the bin value is to be 0.025 minutes. The aforementioned procedure is illustrated in more detail in the subsequent FIG. 2. The principles above also apply to determination of the bin value along the mass-to-charge ratio axis, as illustrated in FIGS. 3A-3E and 4A-4C.

FIG. 2 illustrates application of different bin values in the retention time axis, using the bins 201 having bin values or sizes (hereinafter "bin values") of 0.125 minutes, the bins 211 having bin values of 0.0625 minutes, and bins 221 having bin values of 0.03125 minutes. The bin values may be indicative of, or analogous to, pixel sizes or pixel resolutions. As previously alluded to, higher bin values entail a higher likelihood of loss of signals because in each bin, only a single signal is selected or extracted. To illustrate a concept of signal loss as a result of increasing a bin value, in FIG. 2, applying a bin value of 0.125 minutes, using the bins 201, would result in loss of, or failure to capture, at least the signals 262, 263, 270, 272, 275, 277, and 279. In particular, the signals 262, 263, and 264 would all be within a same bin, and the signal 264 has a higher intensity compared to the signals 262 and 263. Thus, within that bin, only the signal 264 having a highest intensity would be retained. Next, the signals 270 and 269 would both be within a same bin, and the signal 269 has a higher intensity compared to the signal 270. Thus, within that bin, only the signal 269 would be retained. Next, the signals 272 and 273 would both be within a same bin, and the signal 273 has a higher intensity compared to the signal 272. Thus, within that bin, only the signal 273 would be retained. Next, the signals 275 and 276 would both be within a same bin, and the signal 276 has a higher intensity compared to the signal 275. Thus, within that bin, only the signal 276 would be retained. Next, the signals 277 and 278 would both be within a same bin, and the signal 278 has a higher intensity compared to the signal 277. Thus, within that bin, only the signal 278 would be retained. Overall, applying a bin value of 0.125 minutes would result in a loss of seven out of twenty signals, or 35 percent of the signals.

Meanwhile, applying a bin value of 0.0625 minutes would result in a loss of the signals 263, 272, and 275. In particular, the signals 263 and 264, which were previously in the same bin if the bin value were 0.125 minutes, would now be in different bins after decreasing the bin value from 0.125 minutes to 0.0625 minutes. The signals 262 and 263 would still remain in a common bin, and of those two signals only the signal 262 would be retained because the signal 262 has a higher intensity. The signals 269 and 270, which were previously in the same bin if the bin value were 0.125 minutes, would now be in different bins after decreasing the bin value from 0.125 minutes to 0.0625 minutes. Next, the signals 272 and 273 would still remain in a common bin, and of those two signals only the signal 273 would be retained because the signal 273 has a higher intensity. Next, the signals 275 and 276 would still remain in a common bin, and of those two signals only the signal 276 would be retained because the signal 276 has a higher intensity. Next, the signals 277 and 278, which were previously in the same bin if the bin value were 0.125 minutes, would now be in different bins after decreasing the bin value from 0.125 minutes to 0.0625 minutes. Lastly, the signals 279 and 280, which were previously in the same bin if the bin value were 0.125 minutes, would now be in different bins after decreasing the bin value from 0.125 minutes to 0.0625 minutes. Overall, three out of 20 signals would be lost at a bin value of 0.0625 minutes.

Meanwhile, applying a bin value of 0.03125 minutes would result in a loss of the signal 263. The signals 262 and 263 would still remain in a common bin, and of those two signals only the signal 262 would be retained because the signal 262 has a higher intensity. The signals 272 and 273 would be separated into different bins as a result of decreasing the bin value from 0.0625 to 0.03125 minutes. The signals 275 and 276 would also be separated into different bins as a result of decreasing the bin value from 0.0625 to 0.03125 minutes. Overall, one out of 20 signals would be lost at a bin value of 0.03125 minutes. By further reducing the bin value to 0.015625 minutes, the signals 262 and 263 may be separated into different bins. In that scenario, doubling the bin value from 0.015625 to 0.03125 minutes would result in an additional, or marginal, loss of signals at a proportion of five percent, or one in twenty signals. If such an additional loss satisfies or falls within a permitted threshold, then the bin size may be determined to be 0.015625 minutes. Otherwise, if such an additional loss fails to satisfy, or falls outside of a permitted threshold, then the bin size may be determined to be 0.0078125 minutes, because by increasing the bin value from 0.0078125 minutes to 0.015625 minutes, no additional signals would be lost. This process described above, as applied to a single data sample, may be repeated for all other data samples. As will be subsequently described with respect to FIGS. 5A-5F, an image-based representation of the data samples (e.g., the data samples 121, 122, 123, and other data samples) may be generated using the determined bin value along the retention time axis, and along the mass-to-charge ratio axis, as will be illustrated in FIGS. 3A-3E and 4A-4C. From the image-based representation, the computing component 111 may then determine frequencies of occurrence of local maxima, in each bin, across all the data samples.

Figure 3A:
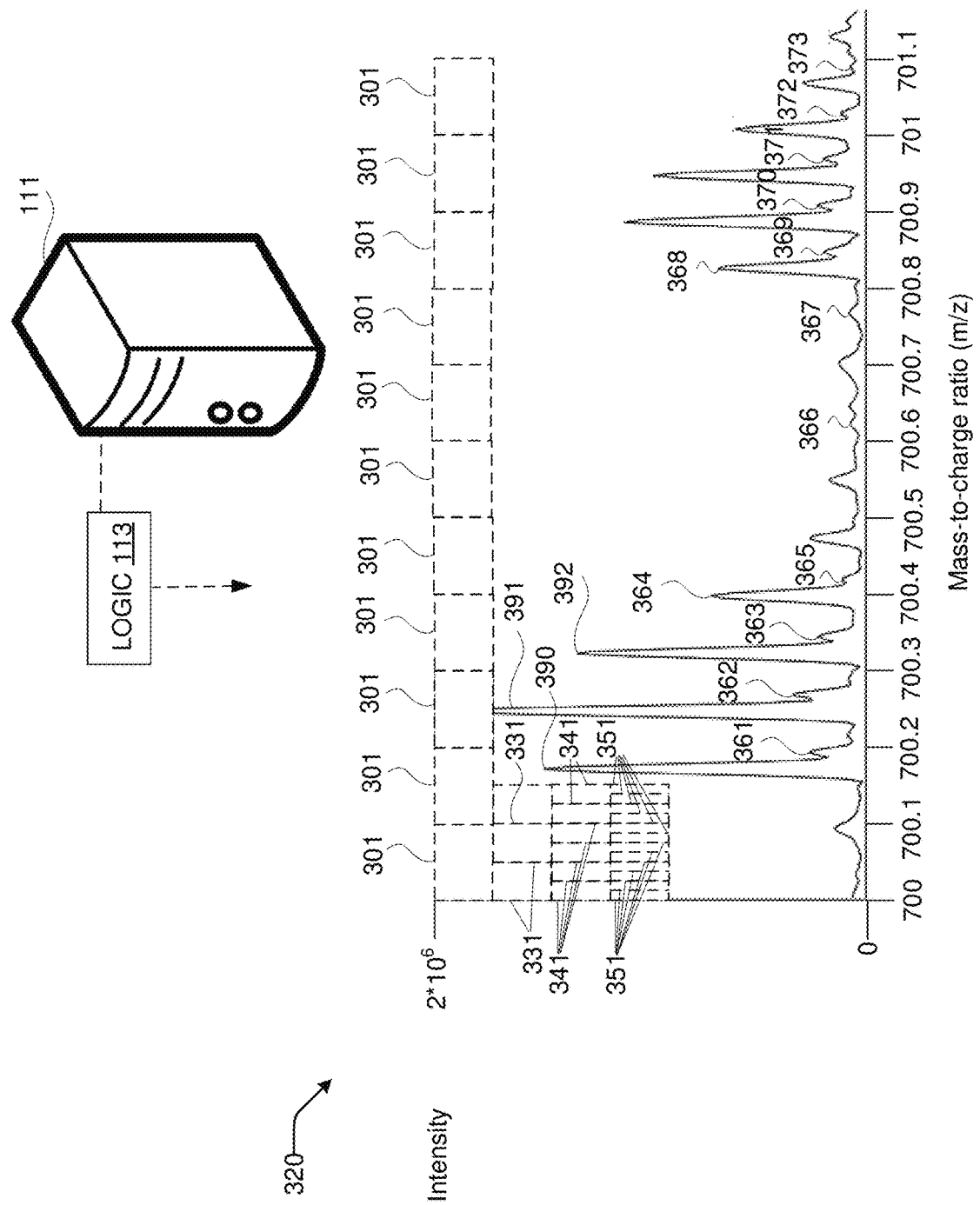
FIG. 3A is an exemplary illustration of a computing component that determines bin values and applies bin values in a mass spectrum, illustrating signal intensities along a mass-to-charge ratio dimension or axis.

FIG. 3A illustrates a mass spectrum 320, which depicts signal intensities as a function of mass-to-charge ratios at a particular retention time. In FIG. 3A, bins 301 have a bin value of 0.1. Meanwhile, bins 331 have a bin value of 0.05; bins 341 have a bin value of 0.025; bins 351 have a bin value of 0.0125. As previously alluded to, only a single signal is selected or extracted within each bin, thereby likely resulting in loss of signals at higher bin values. To illustrate a concept of signal loss as a result of increasing a bin value, in FIG. 3A, a bin value of 0.1 would result in loss of, or failure to capture, at least signals 361-373 because the signals 361-373 are not highest intensity signals within the respective bins, and the computing component 111 obtains or retrieves the local maximum, or the highest intensity signal, in each of the bins. For example, the signal 361 is not a highest intensity signal within the bin between 700.1 and 700.2 because a signal 390 has a higher intensity compared to the signal 361 in that bin. Moreover, the signal 362 is not a highest intensity signal within the bin between 700.2 and 700.3 because a signal 391 has a higher intensity compared to the signal 361 in that bin. Additionally, neither the signal 363 nor the signal 364 is a highest intensity signal within the bin between 700.3 and 700.4 because a signal 392 has a higher intensity compared to the signals 363 and 364 in that bin. Similar reasoning applies to the signals 366-373, which are not highest intensity signals within their respective bins. Therefore, if the computing component 111 were to apply or implement a bin value of 0.1, an excessive or unacceptable amount of signal loss may ensue. Thus, the computing component 111 may apply or implement a bin value that is smaller than 0.1.

As alluded to previously, with respect to FIG. 2, the computing component 111 may determine a bin value based on an amount or proportion of signals that would be lost or failed to be captured as a result of increasing the bin value, compared to a previous bin value and/or compared to an original number of signals. Alternatively or additionally, the computing component 111 may determine a bin value based on an amount or proportion of signals that would be gained, or additionally captured, as a result of decreasing the bin value, compared to a previous bin value. Any principles described above regarding binning in the retention time axis may also be applicable to binning in the mass-to-charge ratio axis, and vice versa.

Figure 3B:
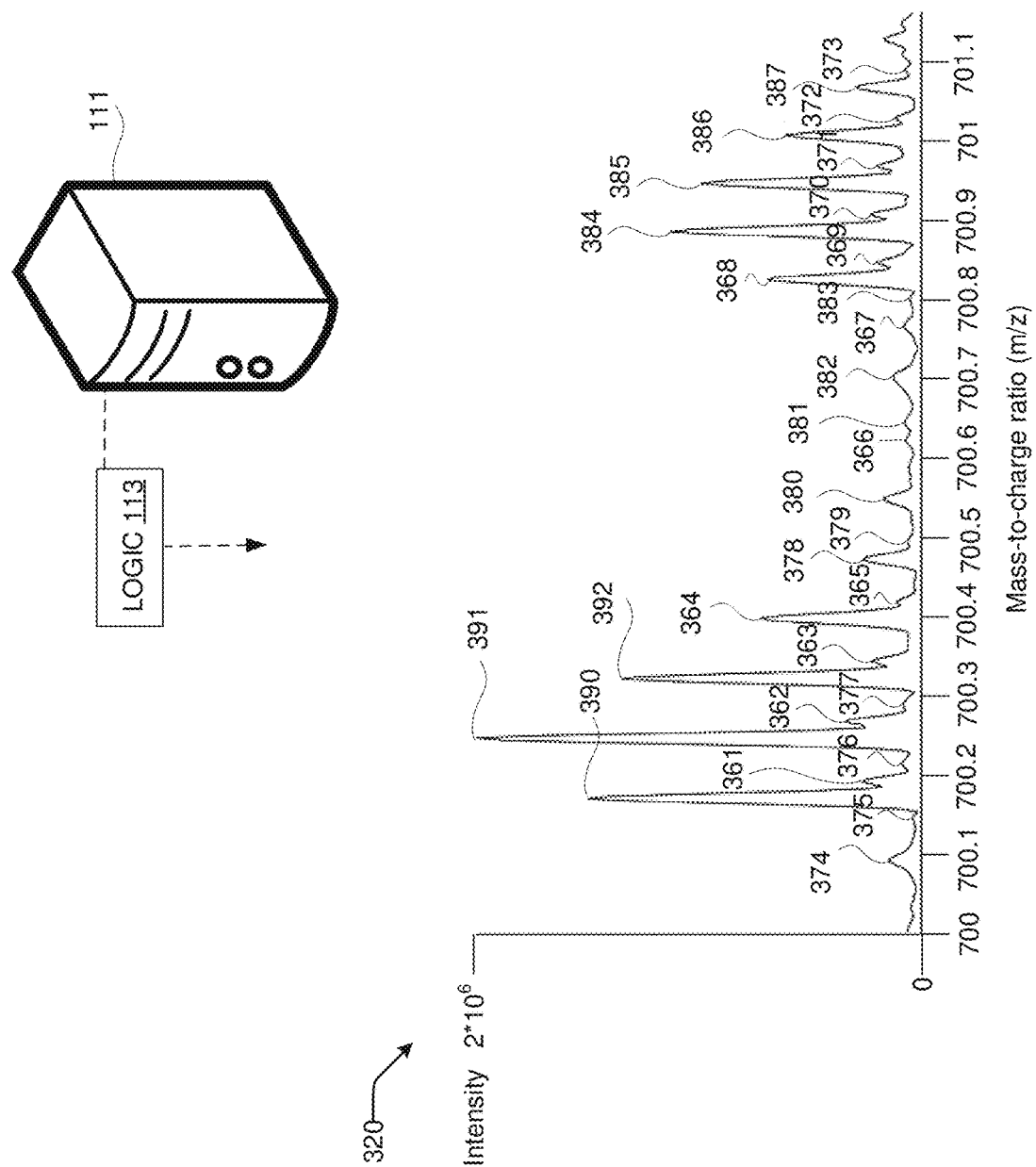
FIG. 3B is an exemplary illustration of a computing component that determines an amount or number of signals detected in a mass spectrum.
Figure 3C:
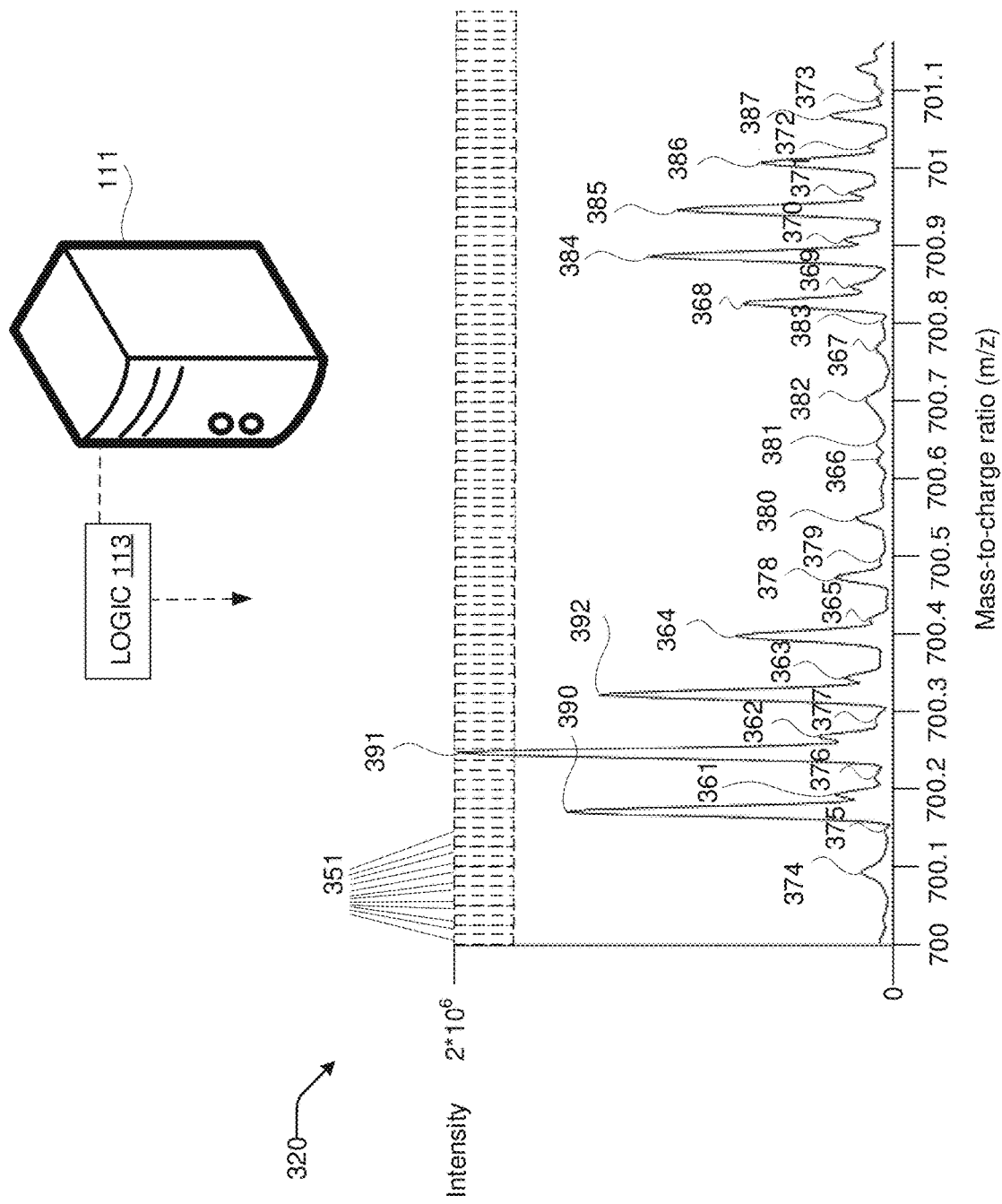
Figure 3E:
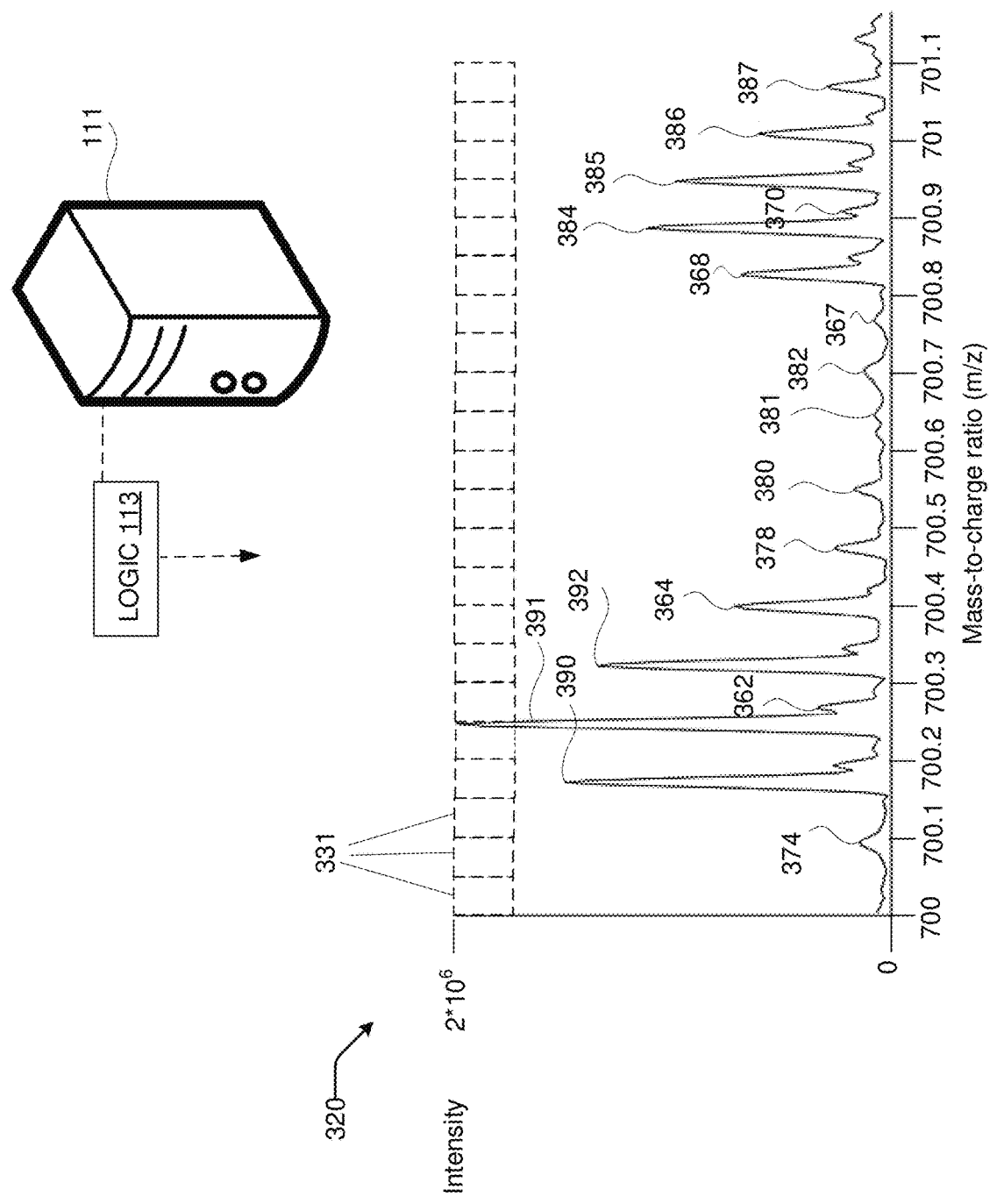

FIG. 3B illustrates signals that would be detected between the mass-to-charge ratios of 700 and 701.1, without binning. The signals include the aforementioned signals 361-373 and the signals 390-392, and signals 374-387, which equates to a total of 30 signals. Meanwhile, FIG. 3C illustrates signals that would be detected at a bin value of 0.0125, using the bins 351. Using a bin value of 0.0125 would still result in detection of all 30 signals previously illustrated in FIG. 3B. FIG. 3D illustrates signals that would still be detected at a bin value of 0.025, using the bins 341. Using a bin value of 0.0125 would result in loss of signals 375, 379, and 371 because of other signals that have higher intensities in the respective bins. In particular, the signal 375 is in a bin between 700.15 and 700.175, and the signal 390 has a higher intensity in that bin. The signal 379 is in a bin from 700.475 to 700.5, and the signal 378 has a higher intensity in that bin. The signal 371 is in a bin from between 700.95 to 700.975, and the signal 385 has a higher intensity in that bin. Thus, changing the bin value to 0.025 would result in a loss of 3 signals, a proportion of ten percent compared to the 30 signals using the bin value of 0.0125. FIG. 3E illustrates signals that would still be detected at a bin value of 0.05 (e.g., using the bins 331). Using the bins 331 would result in loss of signals 361, 376, 377, 363, 365, 366, 383, 369, 372, and 373 compared to using the bins 341. Thus, changing the bin value to 0.05 would result in a loss of 10 signals, or a proportion of $10/27$ or 37%.

Using a bin value of 0.05, the signals 361, 376, 377, 363, 365, 366, 383, 369, 372, and 373 would be lost because of other signals that have higher intensities in the respective bins. In particular, the signal 361 is in a bin from 700.15 to 700.2. The signal 390 has a higher intensity in that bin. The signal 376 is in a bin from 700.2 to 700.25. The signal 391 has a higher intensity in that bin. The signal 377 is in a bin from 700.25 to 700.3. The signal 362 has a higher intensity in that bin. The signal 363 is in a bin from 700.3 to 700.35. The signal 392 has a higher intensity in that bin. The signal 365 is in a bin from 700.4 to 700.45. The signal 364 has a higher intensity in that bin. The signal 366 is in a bin from 700.6 to 700.65. The signal 381 has a higher intensity in that bin. The signal 383 is in a bin from 700.8 to 700.85. The signal 368 has a higher intensity in that bin. The signal 369 is in a bin from 700.85 to 700.9. The signal 384 has a higher intensity in that bin. The signal 372 is in a bin from 701 to 701.05. The signal 386 has a higher intensity in that bin. The signal 373 is in a bin from 701.05 to 701.1. The signal 387 has a higher intensity in that bin. If the threshold, or permitted loss of signals, is 5%, then the computing component may determine the bin value to be 0.0125, because an increase from the bin value of 0.0125 to 0.025 would result in a 10% loss of signals, which exceeds 5%. If the threshold, or permitted loss of signals, is 10%, then the computing component may determine the bin value to be 0.025, because an increase from the bin value of 0.025 would result in a loss of signals of 10%, which is still within the threshold. In the aforementioned scenarios, the threshold loss of signals corresponds to a difference between numbers of captured signals at two consecutive bin values, differing by some factor, such as 2, 5, or 10. However, the threshold loss of signals may, alternatively, correspond to a difference between a number of captured signals at a particular bin value and an original number of captured signals, such as illustrated in FIG. 3B.

Only one mass spectrometry data sample is illustrated in FIG. 2 and the FIGS. 3A-3E. The computing component 111 may implement the aforementioned procedure across all mass spectrometry data samples (e.g., thousands of samples) and determine an overall signal loss resulting from application of different bin values. The overall signal losses, or an overall proportion of signal losses, determined at different bin values may be compared to an overall threshold to determine a particular bin value to be applied across all mass spectrometry data samples. The same determined bin value may be applied across all samples. Although the foregoing focuses on determine a bin size respective to the mass-to-charge ratio axis, the computing component 111 may apply similar or same principles to determine a bin size respective to the retention time axis as well.

In some examples, when determining the frequencies, the computing component 111 may confirm that the identified local maxima or peaks across different data samples, in a particular bin, correspond to a same signal. Assume that in the bin between 700.225 and 700.25, that a highest intensity signal (e.g., the signal 391) has an intensity of $2*10^6$. The computing component 111 may then determine frequencies, across other data samples, at which a highest intensity signal within the bin between 700.225 and 700.25 matches or corresponds to the signal 391. To determine whether an other signal in another data sample matches the signal 391, the computing component 111 may determine whether the other signal has an intensity within a threshold range of that of the signal 391 (e.g., an intensity of $2*10^6$), within that bin. In some nonlimiting examples, the threshold range may be one percent, five percent, ten percent, 0.1% percent, 0.05% percent, or 0.01% percent.

In some examples, different data samples may have a same signal at slightly different positions or values of mass-to-charge ratios. For example, a same signal may occur at mass-to-charge ratios of 791.5, 791.49999 and 791.49998, which may be in different bins, due to measurement errors of the mass spectrometers, for example. Therefore, when determining frequencies of occurrence, the computing component 111 may expand a window previously bounded by a bin in the retention time axis or a mass-to-charge ratio axis. An amount of expansion may be by a threshold value, range, or proportion, of the mass-to-charge ratio, such as, 0.001, 0.0001, 0.01, or $25*10^{-6}$. The computing component 111 may expand a previous window to include the threshold range. For example, if the threshold value is $25*10^{-6}$, then a window with a bin value of 0.025, between 791.475 and 791.5, would now be adjusted to be between 791.474975 and 791.500025.

Additionally, the computing component 111 may determine a reference value of where an actual signal occurs by taking an average, median, or mode over all data samples that have the actual signal present. For example, if the raw mass spectrometry data samples 122 and 123 have the actual signal present at 791.49999 and 791.49998, respectively, and the raw mass spectrometry data sample 121 has the actual signal present at 791.5, the computing component 111 may use an average or median of 791.5, 791.49999, and 791.49998, or 791.49999, as a reference point for the location or position of the actual signal. Using 791.49999 as a reference point, the computing component 111 may determine that any data sample that has a signal, with a proper intensity, corresponding to a mass-to-charge ratio within the threshold range of 791.49999 has the actual signal present. In other words, any data sample that has a signal of a proper intensity within the threshold value of 791.49999, or which deviates by less than the threshold value from 791.49999, may be determined to correspond to the actual signal.

The computing component 111 may determine and record a particular mass-to-charge ratio and a particular retention time, in each bin. For example, a recorded mass-to-charge ratio, at a particular retention time, may be a mass-to-charge ratio corresponding to a most frequently occurring signal in each mass-to-charge ratio bin. As an illustrative example, the computing component 111 may record the determined mass-to-charge ratio as 700.2332 in the mass-to-charge ratio bin from 700.225 to 700.25. Determining a most frequently occurring signal may further account for the aforementioned threshold values or ranges with respect to intensities and mass-to-charge ratios or retention times. For example, any signals within a threshold range of intensities, and/or within threshold ranges of mass-to-charge ratios or retention times, may be determined to correspond to the same signal. The recorded mass-to-charge ratios may correspond to an average, median, or mode of all common signals determined to correspond to the most frequently occurring signal. For example, if signals at mass-to-charge ratios of 700.2333, 700.2332, and 700.2331 have all been determined to correspond to the most frequently occurring signal, then the determined mass-to-charge ratio may be 700.2332.

In some examples, the computing component 111 may compensate for column aging, which may cause shifts in retention time as a mass spectrometry column changes properties over time. In order to correct for retention time drift or shift, the computing component 111 may identify landmark molecules or constituents that are present, or verified to be present, across all samples, and determine retention time shifts with respect to the landmark molecules over time. The determined retention time shifts with respect to the landmark molecules may be applied to other molecules when adjusting for retention time shifts. The mass-to-charge ratios across all samples of the landmark molecules may remain relatively constant, and the landmark molecules may be isolated or segregated from other signals by at least a threshold interval of retention time. That is, no other signals, or no other signals of greater than some threshold intensity, may be present within the threshold interval of retention time from where the landmark molecule is on the retention time axis.

Figure 5A:
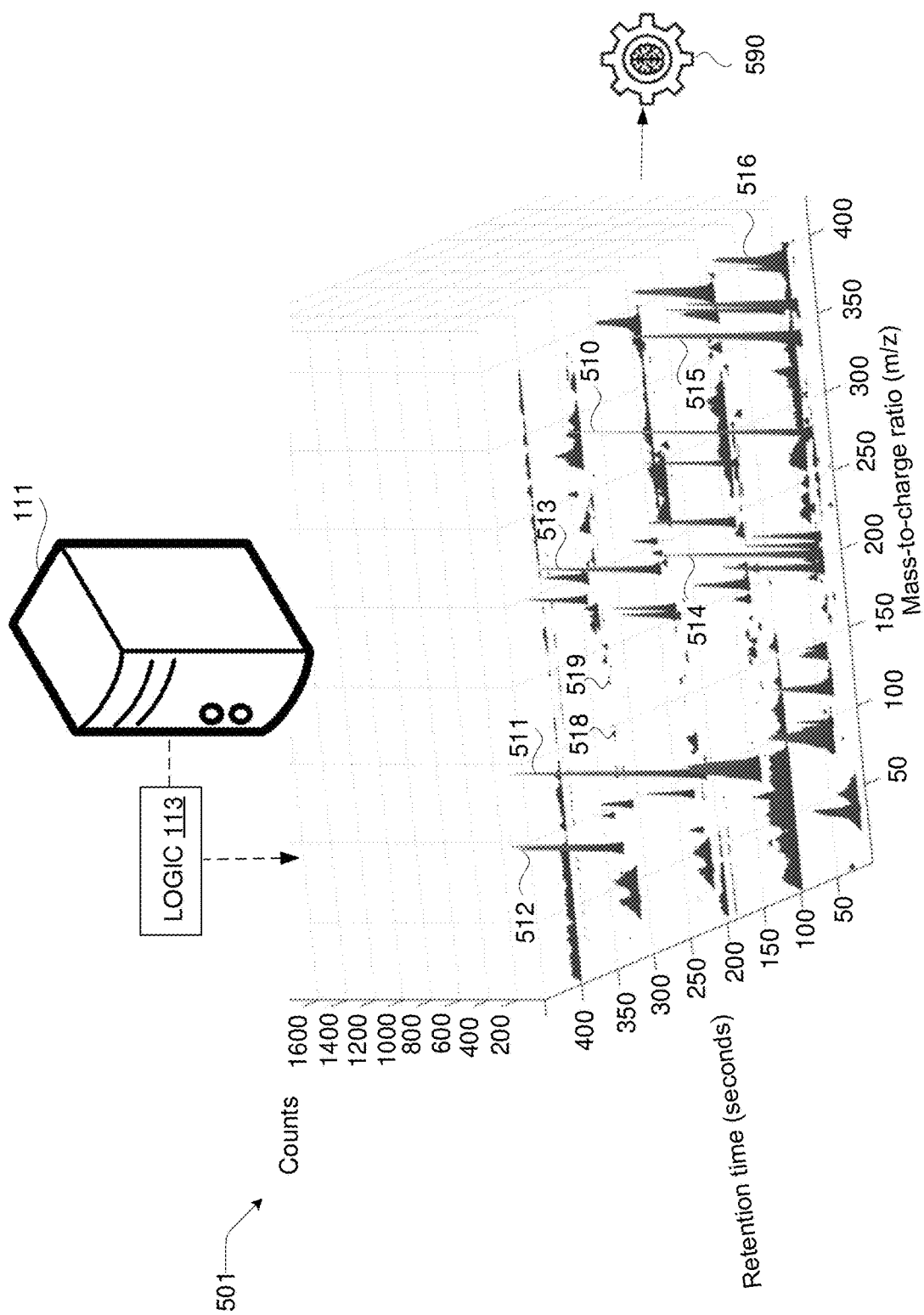
FIG. 5A is an exemplary illustration of a computing component that generates an image-based representation of mass spectrometry data based on frequencies of occurrence of peak signals in each bin.

Upon determining a bin value, the computing component 111 may then convert the data samples (e.g., the data samples 121, 122, 123, and other data samples) into an image format or representation, as illustrated in FIG. 5A, which includes, for each data sample, a single signal in each bin. The image format or representation facilitates further analysis and transformation of the data samples. Each bin, as explained above, may correspond to a given retention time and range of mass-to-charge ratios, or a given mass-to-charge ratio and range of retention times. The computing component 111 may then determine or identify local maxima or peaks in each bin, across all data samples. The computing component 111 may then determine frequencies of occurrence of the local maxima or peaks in each bin across all data samples. For example, if the bin value for mass-to-charge ratio is 0.025, the computing component 111 may determine a single highest intensity signal, or peak (hereinafter "signal") in a bin between 700 and 700.025, a second single highest intensity signal in a bin between 700.025 and 700.05, a third single highest intensity signal in a bin between 700.05 and 700.075, and so on, for a given data sample. The determination of the highest intensity signal may include determining a particular mass-to-charge ratio and an intensity. The computing component 111 may then determine frequencies, across all data samples, at which respective highest intensity signals occur.

Figure 4A:
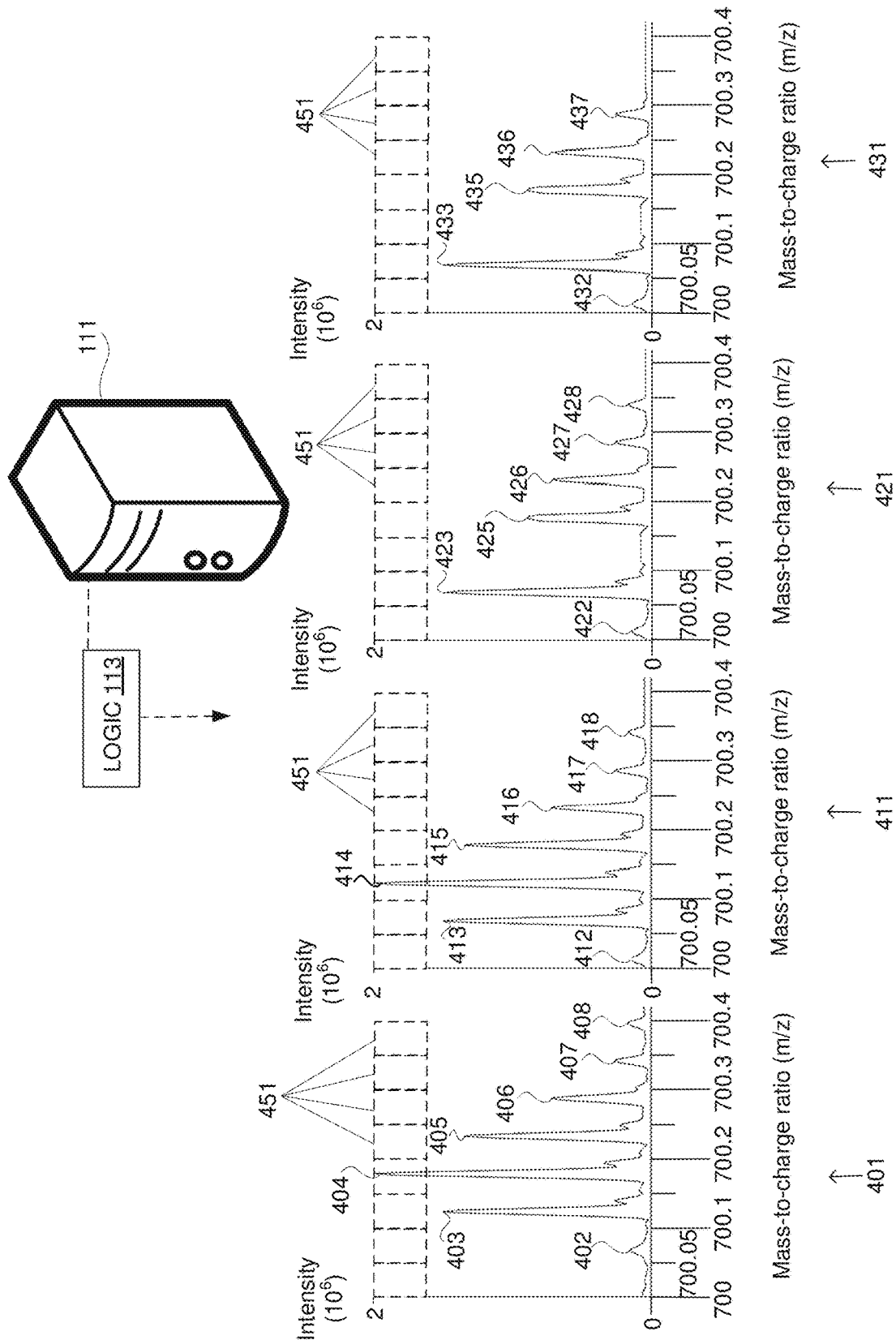

To further illustrate the concept of determining frequencies, in an example illustration of FIG. 4A, the computing component 111 may obtain multiple mass spectrometry data samples, including a first mass spectrometry data sample 401, a second mass spectrometry data sample 411, a third mass spectrometry data sample 421, and a fourth mass spectrometry data sample 431. Each of the first mass spectrometry data sample 401, the second mass spectrometry data sample 411, the third mass spectrometry data sample 421, and the fourth mass spectrometry data sample 431 may be implemented as, or similar to, the mass spectrum 320 of any of FIGS. 3A, 3B, 3C, 3D, and 3E. The computing component 111 may determine a total count of signals in each individual bin, across all the aforementioned mass spectrometry data samples. Although FIGS. 4A-4C illustrate mass spectrums, which include data along the mass-to-charge ratio axis, the concepts described are equally applicable to extracted ion chromatograms, as illustrated in FIGS. 3A-3E.

In FIG. 4A, the computing component 111 may apply bins 451 having a bin value, with respect to a mass-to-charge ratio axis, of 0.05, to each of the aforementioned mass spectrometry data samples. Using the bins 451, the computing component 111 determines that in the first mass spectrometry data sample 401, a signal 402 exists in a bin between mass-to-charge ratios of 700.05 and 700.1, a signal 403 exists in a bin between mass-to-charge ratios of 700.1 and 700.15, a signal 404 exists in a bin between mass-to-charge ratios of 700.15 and 700.2, a signal 405 exists in a bin between mass-to-charge ratios of 700.2 and 700.25, a signal 406 exists in a bin between mass-to-charge ratios of 700.25 and 700.3, a signal 407 exists in a bin between mass-to-charge ratios of 700.3 and 700.35, and a signal 408 exists in a bin between mass-to-charge ratios of 700.35 and 700.4.

Next, the computing component 111 determines that in the second mass spectrometry data sample 411, a signal 412 exists in the bin between mass-to-charge ratios of 700 and 700.05, a signal 413 exists in the bin between mass-tocharge ratios of 700.05 and 700.1, a signal 414 exists in the bin between mass-to-charge ratios of 700.1 and 700.15, a signal 415 exists in the bin between mass-to-charge ratios of 700.15 and 700.2, a signal 416 exists in the bin between mass-to-charge ratios of 700.2 and 700.25, a signal 417 exists in the bin between mass-to-charge ratios of 700.25 and 700.3, and a signal 418 exists in the bin between mass-to-charge ratios of 700.3 and 700.35.

Next, the computing component 111 determines that in the third mass spectrometry data sample 421, a signal 422 exists in the bin between mass-to-charge ratios of 700 and 700.05, a signal 423 exists in the bin between mass-to-charge ratios of 700.05 and 700.1, a signal 425 exists in the bin between mass-to-charge ratios of 700.15 and 700.2, a signal 426 exists in the bin between mass-to-charge ratios of 700.2 and 700.25, a signal 427 exists in the bin between mass-to-charge ratios of 700.25 and 700.3, and a signal 428 exists in the bin between mass-to-charge ratios of 700.3 and 700.35.

Next, the computing component 111 determines that in the fourth mass spectrometry data sample 431, a signal 432 exists in the bin between mass-to-charge ratios of 700 and 700.05, a signal 433 exists in the bin between mass-to-charge ratios of 700.05 and 700.1, a signal 435 exists in the bin between mass-to-charge ratios of 700.15 and 700.2, a signal 436 exists in the bin between mass-to-charge ratios of 700.2 and 700.25, and a signal 437 exists in the bin between mass-to-charge ratios of 700.25 and 700.3.

The computing component 111 may obtain a sum of occurrences, or frequencies, of signals in each bin across all the samples (e.g., the first mass spectrometry data sample 401, the second mass spectrometry data sample 411, the third mass spectrometry data sample 421, and the fourth mass spectrometry data sample 431, in addition to other data samples). The computing component 111, in each bin corresponding to a particular sample, may count at most one signal (e.g., a peak, or highest, intensity signal). In particular, from the four mass spectrometry data samples 401, 411, 421, and 431 illustrated in FIG. 4A, the computing component 111 may determine an existence of a total of three signals in the bin between mass-to-charge ratios of 700 to 700.05, from the signals 412, 422, and 432, a total of four signals in the bin between mass-to-charge ratios of 700.05 to 700.1, from the signals 402, 413, 423, and 433, a total of two signals in the bin between mass-to-charge ratios of 700.1 to 700.15, from the signals 403 and 414, a total of four signals in the bin between mass-to-charge ratios of 700.15 to 700.2, from the signals 404, 415, 425, and 435, a total of four signals in the bin between mass-to-charge ratios of 700.2 to 700.25, from the signals 405, 416, 426, and 436, a total of four signals in the bin between mass-to-charge ratios of 700.25 to 700.3, from the signals 406, 417, 427, and 437, a total of three signals in the bin between mass-to-charge ratios of 700.3 to 700.35, from the signals 407, 418, and 428, and a total of one signal in the bin between mass-to-charge ratios of 700.35 to 700.4, from the signal 408. In some examples, the computing component 111 may determine that within the bin between 700.05 and 700.1, the signal 402 does not correspond to or match the signals 413, 423, and 433 due to differences in intensity between the signal 402 and the signals 413, 423, and 433. Thus, even though the signal 402 is a local maximum within the bin between 700.05 and 700.1 for the sample 401, the signal 402 does not match or correspond to other signals in the same bin between 700.05 and 700.1 for the other samples 411, 421, and 431. Thus, the signal 402 may not be counted. In some examples, the computing component 111 may determine a frequency of signals that exist across all samples in each bin, as described above, and generate an image representation of such. In such a scenario, the computing component 111 may generate a frequency plot 471, as shown in FIG. 4B, illustrating frequencies in each bin as determined above. The frequencies may be illustrated halfway between each bin (e.g., at 700.025 for the bin between 700 and 700.05), at either endpoint of each bin (e.g., at 700 or 700.05), or at any suitable location within each bin.

In alternative examples, the computing component 111 may additionally determine some statistical measure of the mass-to-charge ratios of the signals that exist. For example, the computing component 111 may determine an average, such as a weighted or overall average, median, or mode, of the mass-to-charge ratios of the samples in each bin. For example, if the signal 412 has a mass-to-charge ratio of 700.01, the signal 421 has a mass-to-charge ratio of 700.02, and the signal 431 has a mass-to-charge ratio of 700.015, then the computing component 111 may determine that an average of the three mass-to-charge ratios would be 700.015. In such a scenario, the computing component 111 may generate a frequency plot 481, as illustrated in FIG. 4C, which may illustrate a frequency of three along a y-coordinate and a x-coordinate corresponding to the previously determined average mass-to-charge ratio of 700.015.

FIG. 5A illustrates a result of the computing component 111 generating an image-based representation 501. The image-based representation depicts frequencies or counts of signals across the data samples (e.g., the data samples 121, 122, 123, and other data samples) in each retention time bin and/or mass-to-charge ratio bin. Heights of each of the peaks indicate a frequency or count in which the signals appear across all data samples.

Figure 5B:
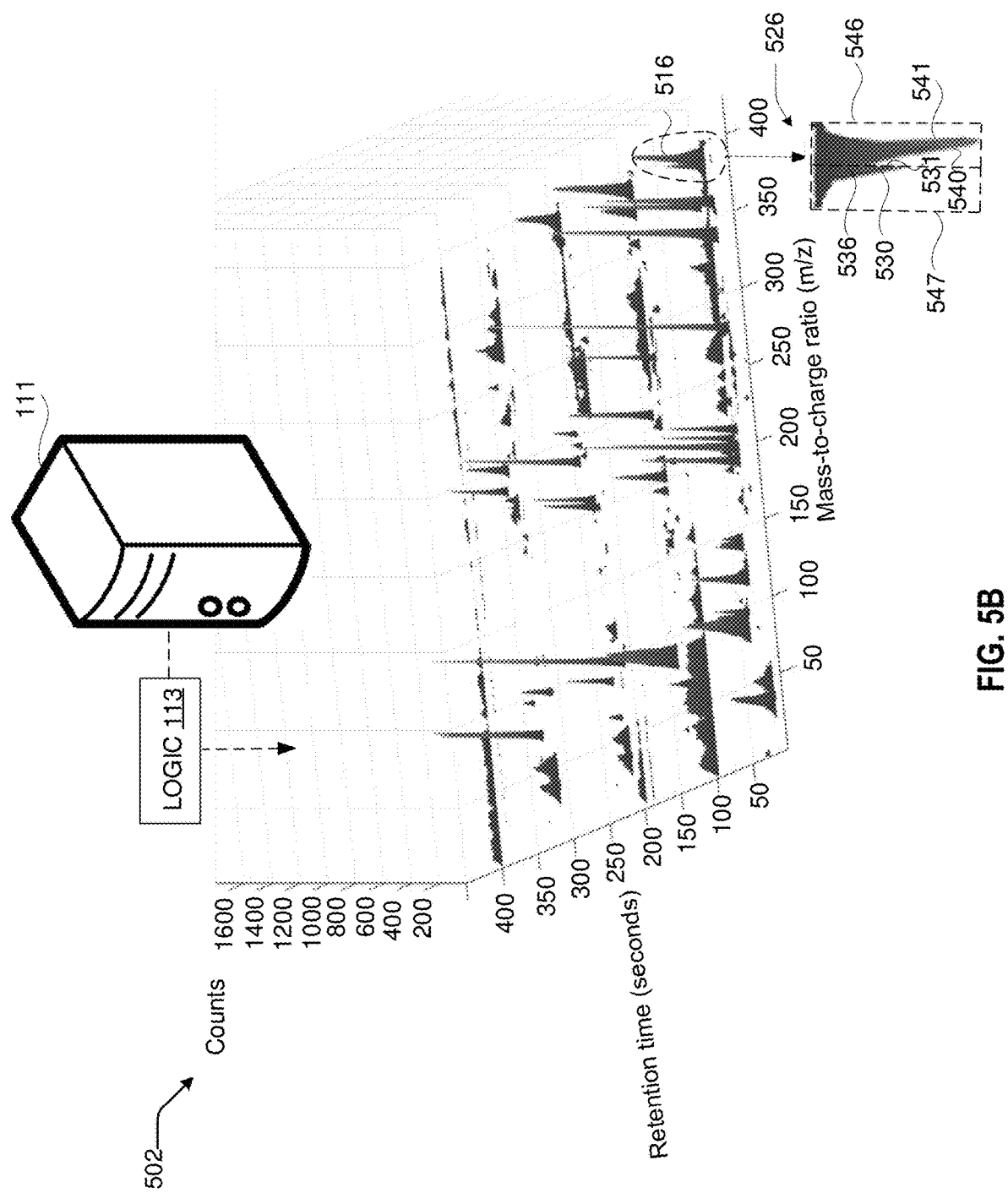
FIG. 5B is an exemplary illustration of a computing component that performs filtering, such as threshold-based filtering, of the image-based representation.

In FIG. 5A, signals of particular high frequency appear around a mass-to-charge ratio of 275 and a retention time of 30 seconds, and around a mass-to-charge ratio of 100 and a retention time of 140 seconds, denoted as peaks 510 and 511, respectively. The computing component 111 may extract a subset of peaks that correspond to a frequency that satisfies a threshold, while discarding or removing a remainder of the signals. The threshold may be defined either in terms of data samples or a proportion of data samples As merely an illustrative example, extracted peaks by the computing component 111 may include the peaks 510 and 511, as well as peaks 513, 514, 515, and 516. As another example, peaks 518 and 519, which correspond to relatively low frequencies or counts, may be among peaks that are discarded. FIG. 5B illustrates a filtered image-based representation 502, in which the peaks 518 and 519 have been filtered out. Only peaks 518 and 519 have been illustrated as filtered out for simplicity; any peaks that fail to satisfy a threshold frequency or count may be filtered out.

In some examples, a threshold proportion of data samples may be ten percent or a threshold number of samples may be 100. Thus, if one of the peaks indicates that less than ten percent of all data samples have a corresponding signal within a particular bin, meaning that the corresponding signal is absent from over ninety percent of all data samples, then the computing component 111 may remove or filter out that peak and disregard any signals that are actually present in the less than ten percent of all data samples. However, otherwise, if ten percent or more of all data samples have the corresponding signal, then the computing component 111 may retain the peak and the corresponding signal that is present in all data samples. Such a filtering procedure may be a first step in removing noise because if a signal is present in a small proportion or number of samples, such a signal is more likely to constitute noise.

The computing component 111 may then perform further segmentation, smoothening, filtration, characterization, and/or labelling of the extracted peaks and feed the results into a machine learning component or model (e.g., a machine learning model 590). The machine learning model may include a neural network classifier or any other supervised or non-supervised machine learning algorithm.

During a process of segmentation, signals that appear close together, for example, which have respective mass-to-charge ratios and/or retention times within threshold ranges of one another, may be distinguished. The computing component 111 may distinguish between two signals by inverting the signals and determining whether the two signals have separate falling and rising edges, and/or a demarcation. In particular, as illustrated in FIG. 5B, the peak 516 may be inverted to form an inverted peak 526. The computing component 111 may determine that the inverted peak 526 includes separate rising and falling edges, such as a first falling edge 530 and a second falling edge 540, and a first rising edge 531 and a second rising edge 541. Additionally the computing component 111 may determine a demarcation or boundary 536. Thus, the computing component 111 may determine that the peak 516 is actually separated into two distinct peaks 546 and 547. In such a manner, the computing component 111 may distinguish between two separate peaks, or verify an existence of two separate peaks, as in the example of the peak 516.

Figure 5C:
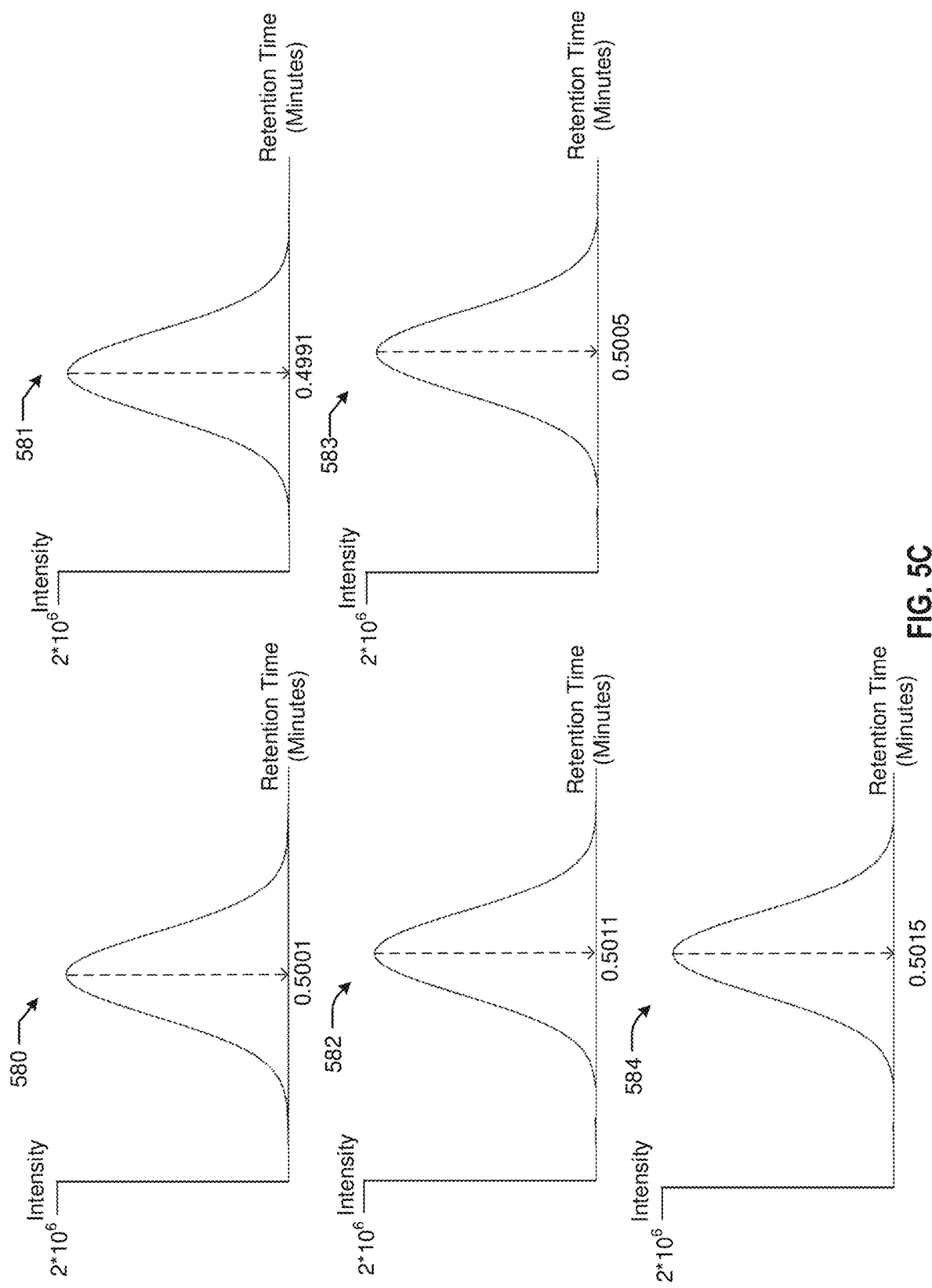
FIG. 5C is an exemplary illustration of a scenario in which retention times vary among samples and are estimated across the samples.

In FIG. 5C, following the identification of peaks, the computing component 111 may perform determination or estimation of retention times over all samples. Due to drift, inherent unique instrument characteristics, and interactions of compounds, retention times may not exactly align across all samples. Therefore, the computing component 111 may obtain an average time at which respective portions of the samples, a compound, or a substance has eluted. This average time may be a weighted centroid or a statistical center, in which half of retention times of the samples are less than the average time and half of retention times of the samples are greater than the average time. A retention time for a single sample may correspond to or be defined by a peak, or local maximum, on an extracted ion chromatogram. To determine retention times across the samples, the computing component 111 may first identify particular bins from the filtered image-based representation 502 that correspond to retention times, at which respective portions of the samples have eluted. For example, the computing component 111 may determine particular retention time bins in which the peak 546 resides by determining positions, along the retention time axis, of the first rising edge 531, the second rising edge 541, and the boundary 536. As an illustrative example, assume that each retention time bin value is 0.001 minutes, and the particular bins identified may be from 0.499 to 0.5, 0.5 to 0.501, and 0.501 to 0.502. The computing component 111, in FIG. 5C, may determine respective positions of retention time peaks within those bins to be 0.5001, 0.4991, 0.5011, 0.5005, and 0.5015 for samples 580, 581, 582, 583, and 584, respectively. The computing component 111 may then determine a median, mean, or mode as the statistical average retention time. If the computing component determines a median, then the retention time would be 0.5005 minutes.

In some examples, the computing component 111 may, in each mass-to-charge ratio bin, extract or retrieve a subset of the peak intensity signals across all the data samples. These extracted or retrieved samples may be fed, ingested, or inputted into the machine learning model 590. For example, given a number of data samples, such as 1000 data samples, the computing component 111 may extract peak intensity signals from a portion or proportion thereof, such as 100 data samples or ten percent of the data samples having highest values of peak intensity signals in each mass-to-charge ratio bin. Such an operation, or computation, may involve storage, within the computing component 111 (e.g., within the database 112, the cache 116, and/or other computing storage), of the subset of the peak intensity signals, or a representation thereof. Additionally, the computing component 111 may perform further preparation and operations, such as transformation and analysis, on the stored subset of the peak intensity signals. In some examples, the computing component 111 may not have enough computing storage capacity, such as an amount of memory (e.g., random access memory (RAM)) to store the entire subset across an entire mass-to-charge ratio dimension. Therefore, the computing component 111 may determine an available amount of computing storage capacity and subdivide the process of extracting the subset into batches based on the available amount of computing storage capacity. For example, the computing component 111 may reserve a certain proportion, such as 50 percent, of the available amount of computing storage capacity, and determine a corresponding amount of signals that would consume that proportion of the available amount of computing storage capacity. Thus, if the available amount of computing storage capacity is 100 GB, from which the computing component 111 reserves 50 GB, an amount of signals that consumes 50 GB of storage may be a hundred signals, which may correspond to a mass-to-charge ratio interval of 0.1. The computing component 111 may determine to process each batch in mass-to-charge ratio intervals of 0.1. However, if the available amount of computing storage capacity is 200 GB, the computing component 111 may determine to process each batch in mass-to-charge ratio intervals of 0.2.

Each batch may correspond to a particular interval of mass-to-charge ratios or a particular interval of retention time and mass to charge ratios. A length of the particular interval may be determined based on the available amount of computing storage capacity. For example, if the entire mass-to-charge ratio axis extends from 700 to 1000, in a first batch, the computing component 111 may extract a first subset of peak intensity signals from all samples within a mass-to-charge ratio interval of 700 to 700.1. In a second batch, the computing component 111 may extract a second subset of peak intensity signals from all samples within a mass-to-charge ratio interval of 700.1 to 700.2. In a third batch, the computing component 111 may extract a third subset of peak intensity signals from all samples within a mass-to-charge ratio interval of 700.2 to 700.3. Such a subdivision addresses the problems of extracting a subset of peak intensity signals from all samples within the entire mass-to-charge ratio axis of 700 to 1000 in a single pass, which may overwhelm the computing storage capabilities of the computing component 111. As a result, the process may be versatility applied to any scenario of any amount of available computing storage capabilities within a computer, while conserving time by preventing an excessive number of batches.

Figure 5D:
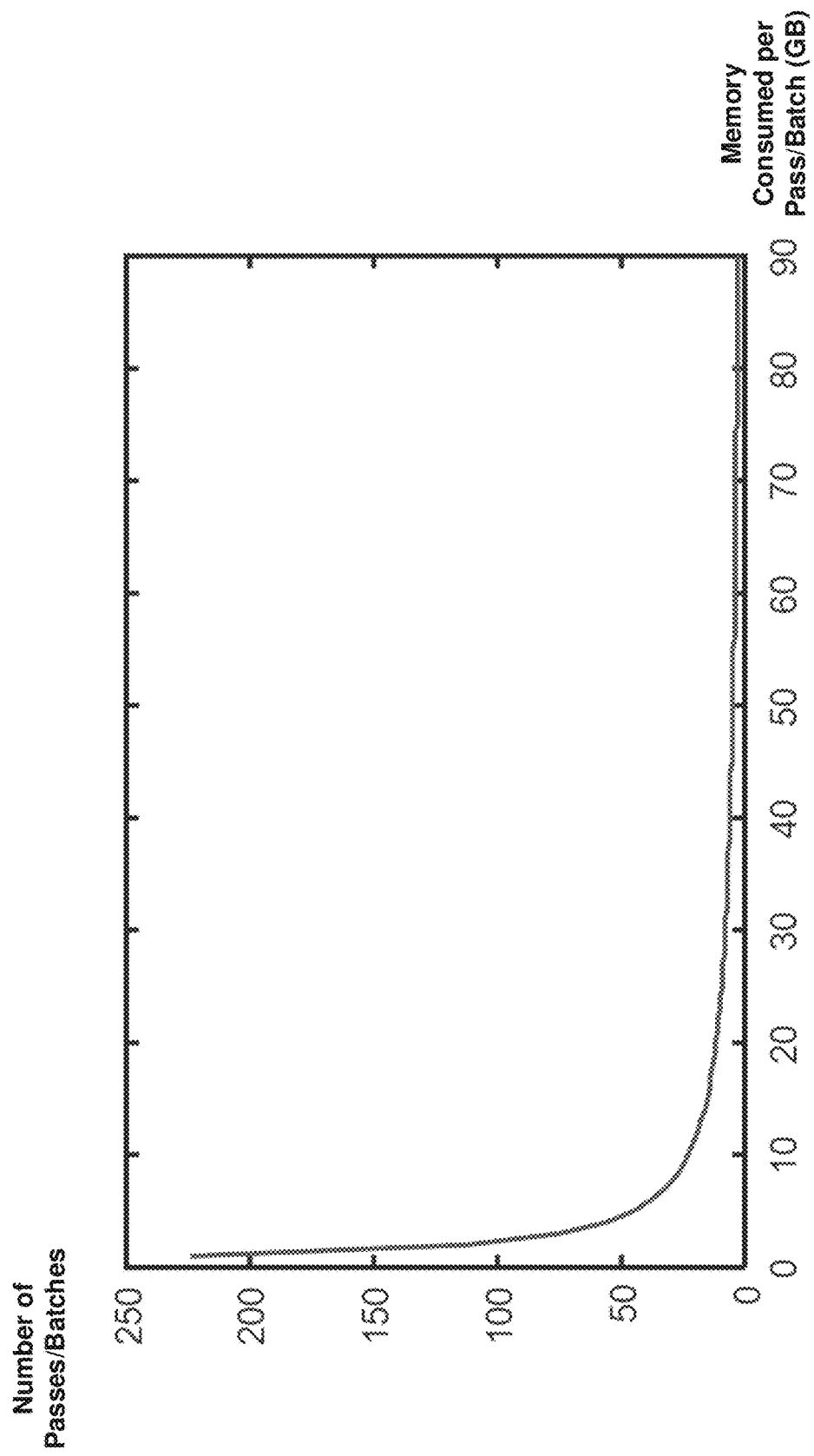
FIG. 5D is an exemplary illustration of a relationship between a number of passes or batches through which a subset of signals is extracted and an amount of memory consumed to store the signals per pass or batch.

To illustrate the problem of extracting from all samples within the entire mass-to-charge ratio axis in a single pass, a total number of signals or peaks, after filtering, may be 1.8 million. Each signal may have a length, such as a number of pixels, of approximately 371. In some examples, each signal may have a length or number of pixels of between 100 and 1000, or between 100 and 500, inclusive. Given 1000 files and 4 bytes to store each unit length of signal, or each pixel, assuming a 32 bit single precision storage, 2.6 terabytes (TB) of data would be needed. If ten percent of the total read data constitutes the subset to be stored, then 0.26 TB of data would be stored. Most computers do not have 0.26 TB of available memory. FIG. 5D illustrates that by increasing a number of batches or passes through the entire mass-to-charge ratio axis, a memory consumed per batch or pass may decrease. For example, if 50 GB of memory is consumed or available, then the computing component 111 may subdivide into ten batches.

Referring back to FIG. 4A, to illustrate the aforementioned subdivision on a smaller scale, the computing component 111 may extract a first subset of peak intensity signals from all samples within a mass-to-charge ratio interval of 700 to 700.1. Thus, the first subset may include the signals 412, 422, and 432 within the bin from 700 to 700.05, if the signals 412, 422, and 432 are among the highest intensity peaks within the bin from 700 to 700.05 when compared across signals of all samples. The first subset may also include the signals 413, 423, and 433 within the bin from 700.05 to 700.1, if the signals 412, 422, and 432 are among the highest intensity peaks within the bin from 700.05 to 700.1 when compared across signals of all samples. Because the signal 402 has a much lower intensity, the signal 402 may not be included within the subset of extracted signals.

In some examples, the selection of the subset of peak intensity signals may be based not only on respective intensities of the extracted signals (e.g., intensities of peaks), but also based on variances or levels of consistency in respective intensities across different samples, shapes and respective variances or levels of consistency in the shapes across different samples, noise within the signals or surrounding noise of signals across different samples, and/or differences in intensities and shapes of signals between first samples that have a particular compound compared to second samples that are missing the particular compound, or in which the particular compound is not prominent. In some examples, the levels of consistency in the shapes may be determined along different points or locations of the signals, such as along rising or falling edges.

The computing component 111 may further remove individual signals corresponding to samples that are outliers and/or determined or predicted to be erroneous or defective. In some examples, the computing component 111 may remove any signals in which a sample has a lower than a first threshold intensity and retain any signals in which a median intensity across all samples exceeds a second threshold intensity. Following the selection of the subset of the peak intensity signals, the computing component 111 may obtain, retrieve, or determine the mass-to-charge ratio and the retention times corresponding to the selected or extracted peak intensity signals. In some examples, the computing component 111 may already have determined mass-to-charge ratios and/or retention times of the respective selected or extracted signals corresponding to each of the bins. The computing component 111 may have recorded the mass-to-charge ratios as metadata, as described with respect to FIGS. 3A-3E. For example, referring back to FIGS. 3A-3E, the computing component 111 may have recorded a specific mass-to-charge ratio of 700.2332 in the mass-to-charge ratio bin from 700.225 to 700.25. If already recorded, the computing component 111 may retrieve the specific mass-to-charge ratio and a specific retention time of each bin corresponding to the selected or extracted peak intensity signals.

Otherwise, if not already recorded, the computing component 111 may determine, via logic, from the selected or extracted signals, a most frequent mass-to-charge ratio and retention time corresponding to each bin, or alternatively, an average, median, or mode of a subset of most frequent mass-to-charge ratios and retention times within particular ranges (e.g., a range of a particular size or magnitude, such as no more than 0.000025, or 25 parts per million). To do so, the computing component 111 may determine, for each sample or for a subset of the samples, a particular mass-to-charge ratio and retention time having a highest value, or local maxima, in each bin. The computing component 111 may then determine highest frequency occurrences of local maxima of the particular mass-to-charge ratio and the particular retention time across all samples. Upon determining the mass-to-charge ratio and the retention time, the computing component 111 may search for occurrences of the local maxima in neighboring bins in order to account for errors or tolerances across the samples. For example, an error in the mass-to-charge ratio dimension may be 25 parts per million.

Figure 5E:
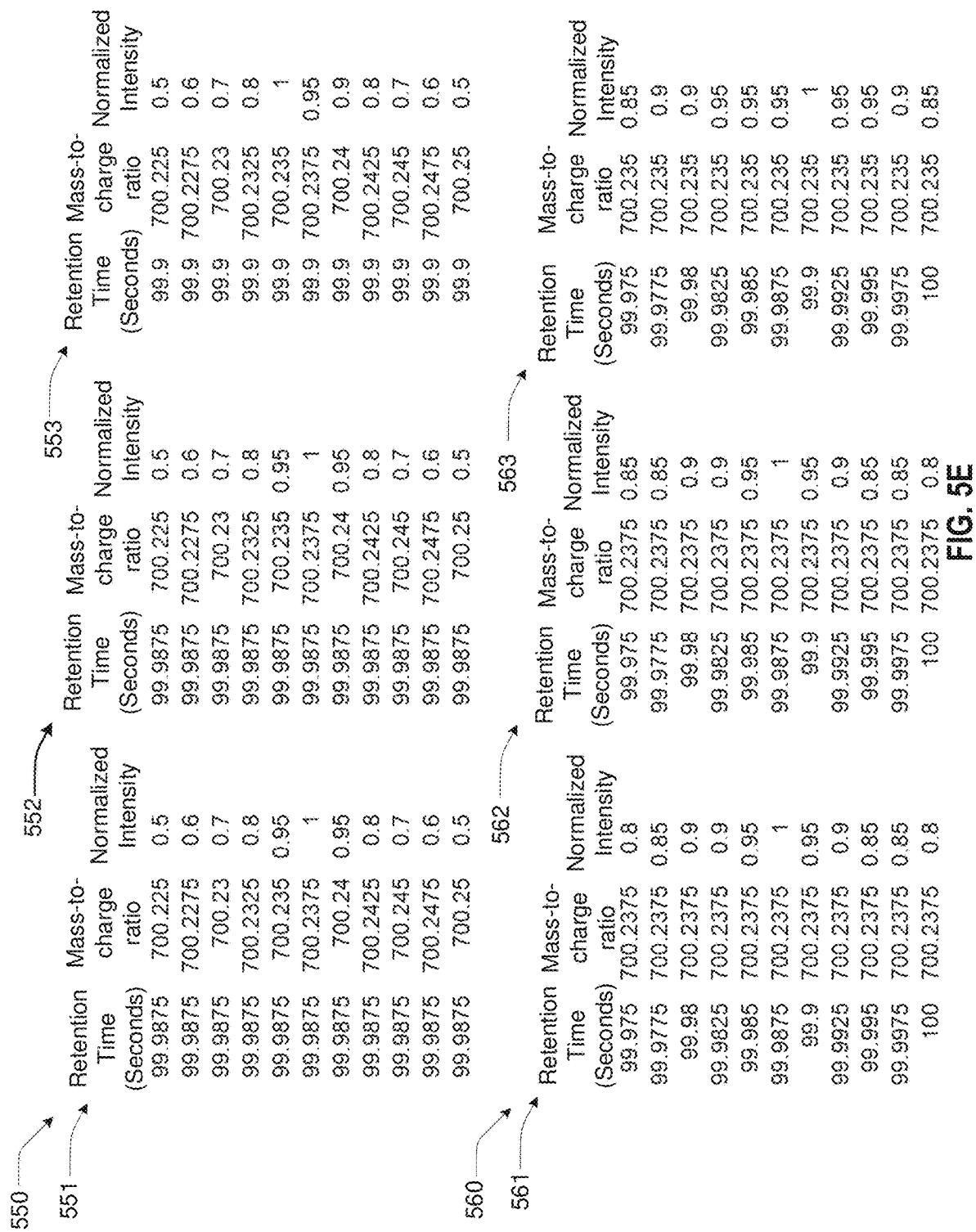
FIG. 5E is an exemplary illustration of a computing component that determines or retrieves a mass-to-charge ratio and retention time corresponding to each distinct signal.

As an illustrative example, in FIG. 5E, a first group 550 of datasets includes a first dataset 551, a second dataset 552, and a third dataset 553 and a second group 560 of datasets includes a fourth dataset 561, a fifth dataset 562, and a sixth dataset 563. Each of the first dataset 551, the second dataset 552, and the third dataset 553 correspond to different samples. Additionally, each of the fourth dataset 561, the fifth dataset 562, and the sixth dataset 563 correspond to different samples. The first dataset 551 and the fourth dataset 561 may correspond to a common sample (e.g., a first sample). The second dataset 552 and the fifth dataset 562 may correspond to a common sample (e.g., a second sample). The third dataset 553 and the sixth dataset 563 may correspond to a common dataset (e.g., a third sample). The first group 550 of datasets may be used to determine a mass-to-charge ratio while the second group 560 may be used to determine a retention time. From the first group 550, the computing component 111 may determine that in the first dataset 551, a local maximum of mass-to-charge ratio, within a mass-to-charge ratio bin of between 700.225 to 700.25, at a retention time of 99.9875 seconds, occurs at 700.2375. The computing component 111 may determine that in the second dataset 552, a local maximum of mass-to-charge ratio, within a mass-to-charge ratio bin of between 700.225 to 700.25, also occurs at 700.2375. The computing component 111 may determine that in the third dataset 553, a local maxima of mass-to-charge ratio, within a mass-to-charge ratio bin of between 700.225 to 700.25, occurs at 700.2375. Therefore, a most frequent occurrence of the local maxima of the mass-to-charge ratio, across the three samples, is at 700.2375, which occurs in two out of three samples, namely, the first sample and the second sample. Meanwhile, the local maximum of the mass-to-charge ratio of 700.235 only occurs in one of the three samples, namely, the third sample.

The computing component 111 may further determine, or refine a determination, of the retention time, given a particular mass-to-charge ratio, using the second group 560. In particular, from the fourth dataset 561, the computing component 111 may determine that at a fixed mass-to-charge ratio of 700.2375, as determined previously for the first sample, the retention time that corresponds to a highest intensity signal, or local maximum, occurs at 99.9875 seconds. Similarly, from the fifth dataset 562, the computing component 111 may determine that at a fixed mass-to-charge ratio of 700.2375, as determined previously for the second sample, the retention time that corresponds to a highest intensity signal, or local maximum, occurs at 99.9875 seconds. Next, from the sixth dataset 563, the computing component 111 may determine that at a fixed mass-to-charge ratio of 700.235, as determined previously for the third sample, the retention time that corresponds to a highest intensity signal, or local maximum, occurs at 99.9 seconds. Therefore, a most frequent occurrence of the local maxima of the retention time, across the three samples, is at 99.9875 seconds, which occurs in two out of three samples, namely, the first sample and the second sample. Meanwhile, the local maximum of the retention time of 99.9 seconds only occurs in one of the three samples, namely, the third sample. Therefore, the computing component 111 may determine that a most frequent occurrence of local maxima is at a retention time of 99.9875 seconds and a mass-to-charge ratio of 700.2375. In some examples, upon such determination, the computing component 111 may retrieve all occurrences of signals that correspond to the determined retention time and the mass-to-charge ratio by searching in bins that include threshold ranges of the retention time and the mass-to-charge ratio. For example, if the error in the mass-to-charge ratio is 25 parts per million, then the mass-to-charge ratio range to account for such error is 700.21 to 700.255. Given a hypothetical bin value of 0.01, then the computing component 111 may search in bins between 700.20 and 700.21, between 700.21 and 700.22, between 700.22 and 700.23, between 700.23 and 700.24, and between 700.24 and 700.25.

In alternative examples, the computing component 111 may determine a particular range of a particular size or magnitude in which the highest frequency of signals occur, compared to other ranges of a same magnitude or size within a particular bin. In some examples, a size of the ranges may be $0.05*10^{-n}$, $0.025*10^{-n}$, or $0.01*10^{-n}$, wherein n may be an integer between 0 and 4, inclusive. For example, the computing component 111 may determine an average, median, or mode of a subset of mass-to-charge ratios in the range from 700.235 to 700.2375, inclusive. In such a range, a highest frequency of signals may occur compared to other ranges of a size of 0.0025 within the mass-to-charge bin from 700.225 to 700.25. Within the subset, all signals corresponding to the most frequent mass-to-charge ratios may have intensities within threshold ranges of one another (e.g., between 0.95 and 1 times that of a particular intensity). Using the example of FIG. 5E again, the computing component 111 may determine that the local maxima of mass-to-charge ratios occur at 700.2375 in two samples and 700.235 in one sample. Because these local maxima are all within a particular range, the computing component 111 may obtain a weighted average, median, or mode of these local maxima. For example, the weighted average of two occurrences of 700.2375 and one occurrence of 700.235 would be approximately 700.2366667. However, if in one sample, a local maxima of mass-to-charge ratio occurs at 700.2275, such a local maxima may occur outside of the particular range, and may be disregarded during determination of the mass-to-charge ratio.

In such a manner, the computing component 111 may identify, characterize, and/or label each of the extracted signals prior to inputting into a machine learning model (e.g., the machine learning model 590). Additionally, the computing component 111 may determine a more accurate value of mass-to-charge ratio, at a higher resolution compared to a range given by the bin value, in order to provide accurate identification of a particular constituent.

Figure 5F:
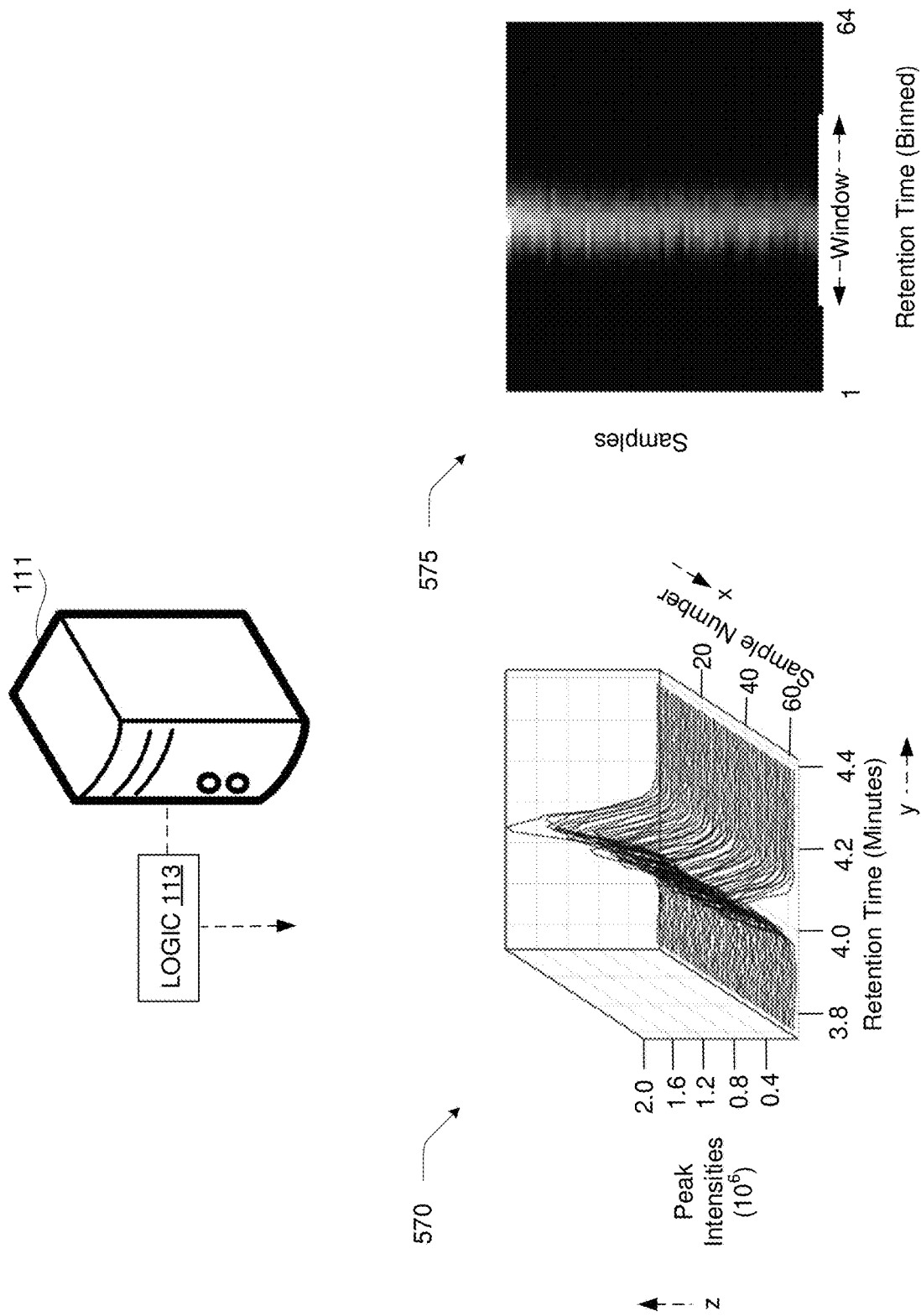
FIG. 5F is an exemplary illustration of a computing component that generates an input for a machine learning model.

A particular representation of an input into the machine learning model 590 is illustrated in FIG. 5F. The computing component 111 may generate a plot 570 that includes intensities along a z-axis corresponding to, or indicating, respective retention times along a y-axis, for each of different samples along a x-axis. Though not illustrated for simplicity, the plot 570, or a separate plot, may also include respective mass-to-charge ratios for each of the different samples. The plot 570, or information from the plot 570, may be transformed into an input 575 that represents a top view, from a perspective of view directly above a xy-plane. Although not illustrated for simplicity, the input 575, or a separate input, may also include respective mass-to-charge ratios for each of the different samples.

The intensities in the input 575 have been converted to image, or color, representations based on a grayscale spectrum. For example, white may represent a highest normalized intensity, such as a normalized intensity of 1, while black may represent or indicate an absence of a signal, a normalized intensity of 0, or a region outside of a window. In some examples, the computing component 111 may receive an input or indication of a particular window. In other examples, the computing component 111 may determine a particular window within which a certain proportion (e.g., a majority or all of) the signals are situated. In some examples, the particular window may be determined based on a subset of samples, and/or based on segmentation. The particular window may be a region in which signals (e.g., peaks, tops, or maxima of the signals) of the subset of the samples are situated or located. The computing component 111 may determine the most frequent mass-to-charge ratio and retention time corresponding to each bin, as described with respect to FIGS. 5A-5D, or alternatively, an average, median, or mode of a subset of most frequent mass-to-charge ratios and retention times within particular ranges, to determine the particular window. In some examples, the particular window may be determined further based on variabilities (e.g., standard deviations) of mass-to charge ratios and retention times corresponding to each bin, or corresponding to a subset of signals from different samples in each bin. The input 575 may include the particular window, which indicates boundaries within which the machine learning model 590 is confined to analyze. The peak intensities may be normalized so that all values of peak intensities vary between zero and one, prior to being fed into the machine learning model. Once fed into the machine learning model, the machine learning model may infer, predict, or determine a veracity of any signals or potential signals within the particular window, with or without examining outside the particular window.

Upon determining or receiving the particular window, the computing component 111 may remove windows that span greater than a threshold amount or interval of retention time, such as, an entire time of retention time for a particular experiment. The computing component 111 may further remove or discard retention time windows that fail to satisfy a threshold number of scans, pixels within the image representation, which may signify sizes or intervals of time, such as three scans. In other words, the computing component 111 may further remove or discard retention time windows that are less than a threshold interval of time. The computing component 111 may further remove or discard windows supported by less than a threshold proportion of samples, such as one percent of samples. Thus, if, within a given retention time window, less than the threshold proportion of samples had a signal, then the computing component 111 may remove or discard that given retention time window.

In some examples, the computing component 111 may expand the particular window, along with other windows, to account for possible stray samples due to retention time shift or drift and/or errors of mass-to-charge ratios. This expansion of windows may occur following selection of a machine learning model (e.g., the machine learning model 590). The machine learning model may remove a subset (e.g., a portion or all) of windows that lack true signal to mitigate or avoid conflicts that otherwise would occur during window expansion.

To expand the particular window with respect to retention time, the computing component 111 may obtain shifted, or offset, plots (hereinafter "shifted plots"), and superimpose or overlay the shifted or offset plots as illustrated in FIGS. 6A-6D. In such a manner, the computing component 111 may expand numerous windows simultaneously rather than expanding each window one-by-one. In particular, in FIG. 6A, the computing component 111 may obtain a plot 610, which may include signals as illustrated in the plot 570 of FIG. 5F, while further including stray signals 614 and 616 and a particular window 612. The stray signals 614 and 616 may be outside boundaries of the particular window 612. The computing component 111 may obtain a first shifted plot 620 after performing a first shift or offset (hereinafter "first shift") 622 by shifting the plot 610 in a positive y-direction, while maintaining the particular window 612 without shifting. The first shift 622 may have a particular interval, size, or number of pixels, which may be determined based on a variability of a subset of the signals in the plot 610. Following the first shift 622, the computing component 111 may overlay, superimpose, or merge an additional region of the first shifted plot 620 that is captured by the particular window 612, which corresponds to an additional region having a particular interval or size of the first shift 622. The additional region was not captured by the particular window 612 when applied to the plot 610. The computing component 111 may disregard any other regions within the particular window 612 of the first shifted plot 620 which have already been captured within the particular window 612 of the plot 610.

Figure 6A:
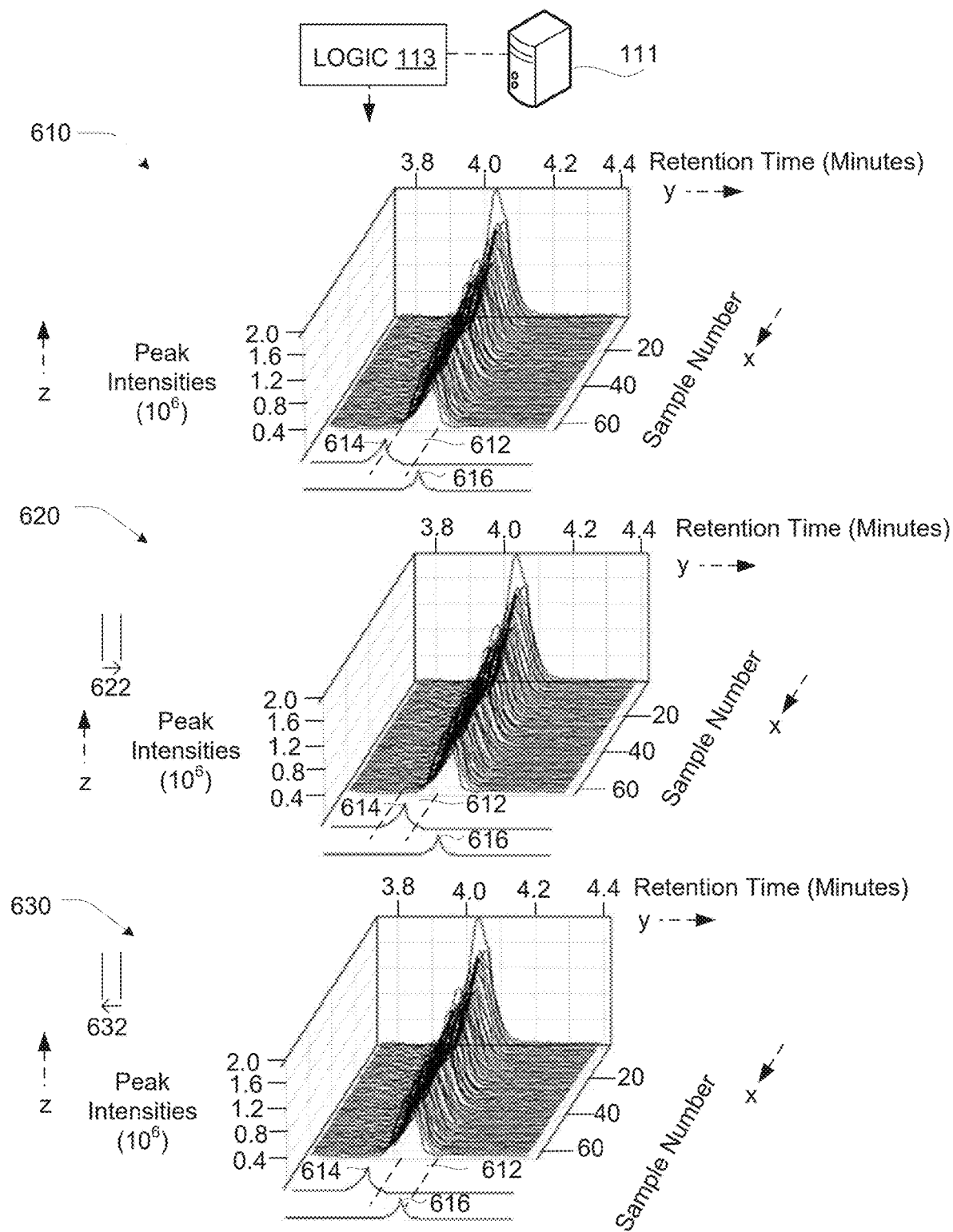
FIGS. 6A-6F are exemplary illustrations of a computing component that expands a window along a retention time axis to capture potentially stray signals.
Figure 6B:
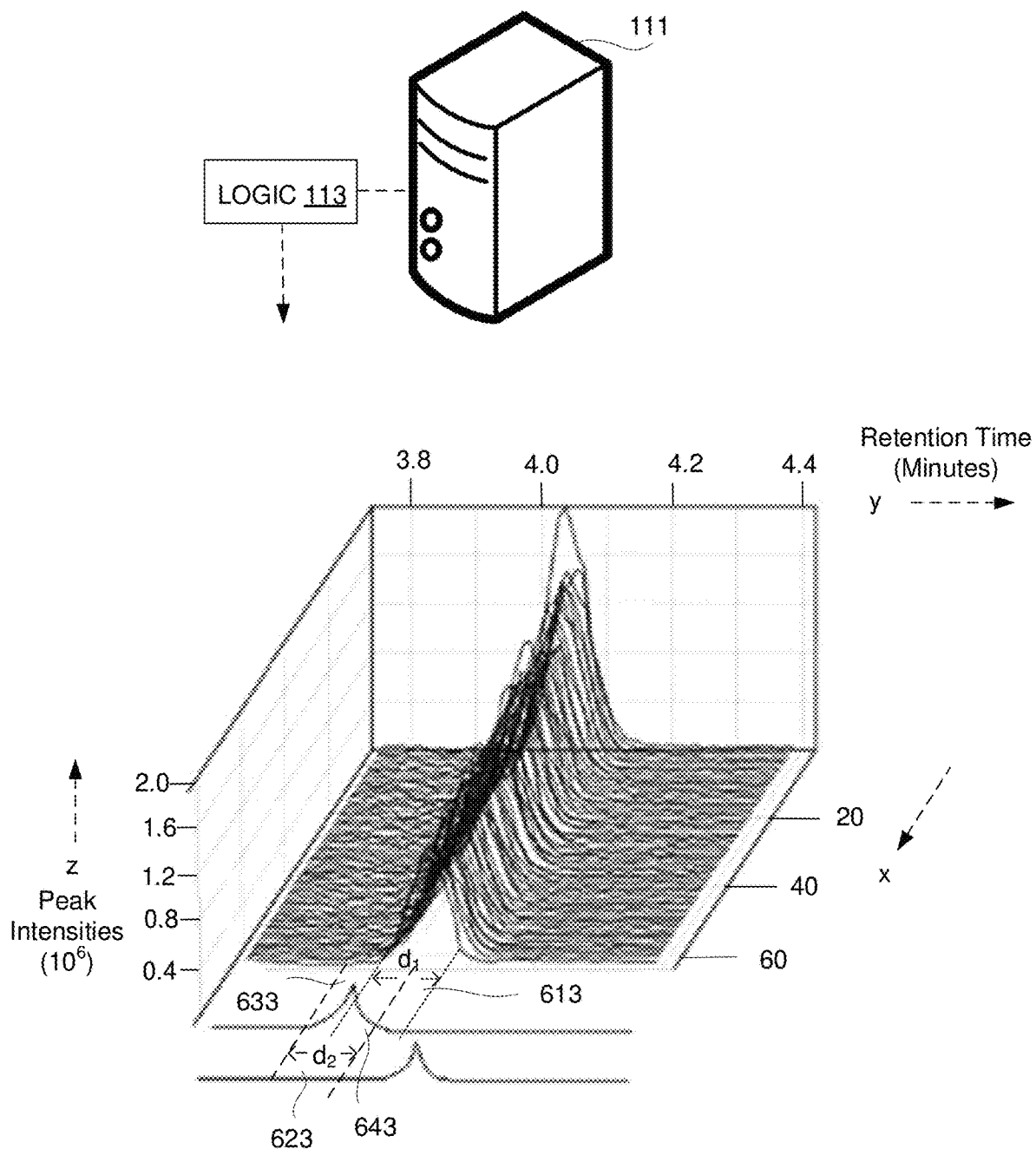

As illustrated in FIG. 6B, the computing component 111 may capture a first region 613 of the plot 610, denoted as $d_1$ and which corresponds to the particular window 612 within the plot 610. Next, the computing component 111 may capture a second region 623 within the plot 610, denoted as $d_2$ and which results when the plot 610 is shifted in the positive y-direction by the first shift 622 while maintaining the particular window 612 without shifting. The second region 623 corresponds to the particular window 612 within the first shifted plot 620. The computing component 111 captures an additional region 633 which is within boundaries of $d_2$ but outside boundaries of $d_1$ while disregarding another region 643 that is common to, or present in, both $d_2$ and $d_1$. In other words, the other region 643 is within the intersection of $d_2$ and $d_1$. Therefore, the first shift 622 of the particular window 612 may increase a region that originally included $d_1$ to further include a region dz. As a result, when applying the particular window 612 to the first shifted plot 620, the computing component 111 may capture the stray signal 614, which was not captured when applying the particular window 612 to the plot 610.

As illustrated in FIG. 6A, the computing component 111 may obtain a second shifted plot 630 after performing a second shift or offset (hereinafter "second shift") 632 by shifting the plot 610 in a negative y-direction, while maintaining the particular window 612 without shifting. The second shift 632 may have a particular interval, size, or number of pixels, which may be the same interval, size, or number of pixels as the first shift 622 but in an opposite direction as the first shift 622. Following the second shift 632, the computing component 111 may overlay, superimpose, or merge a second additional region of the second shifted plot 630 that is captured by the particular window 612, which corresponds to an additional region having a particular interval or size of the second shift 632. The additional region was not captured by the particular window 612 when applied to the plot 610, or to the first shifted plot 620. The computing component 111 may disregard any other regions within the particular window 612 of the second shifted plot 630 which have already been captured within the particular window 612 of the plot 610.

Figure 6C:
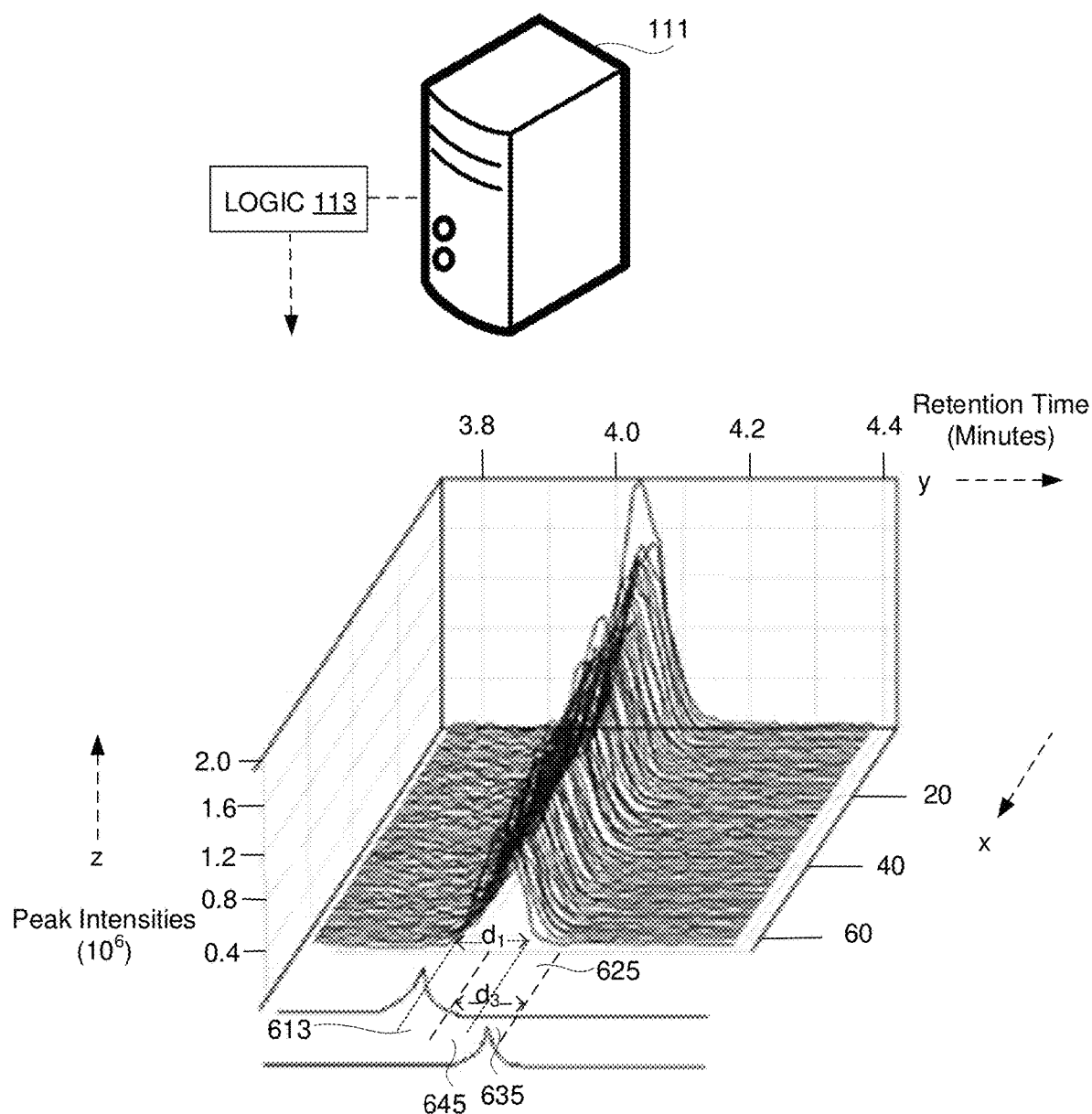
Figure 6D:
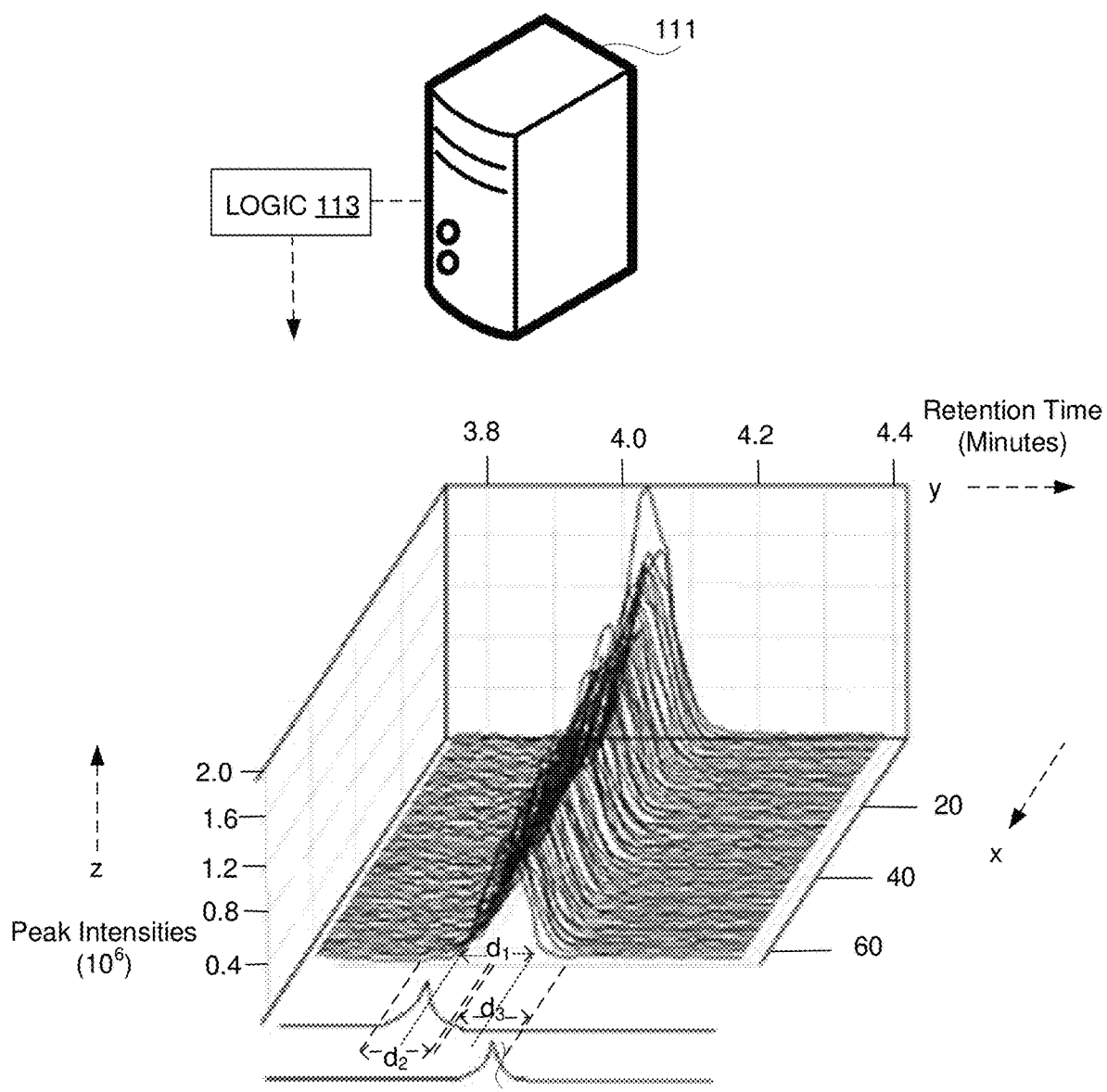

As illustrated in FIG. 6C, the computing component 111 may capture the first region 613 of the plot 610, denoted as $d_1$ and which corresponds to the particular window 612 within the plot 610. Next, the computing component 111 may capture a third region 625 within the plot 610, denoted as $d_3$ and which results when the plot 610 is shifted in the negative-direction by the second shift 632 while maintaining the particular window 612 without shifting. The third region 625 corresponds to the particular window 612 within the second shifted plot 630. The computing component 111 captures an additional region 635 which is within boundaries of $d_3$ but outside boundaries of $d_1$ while disregarding another region 645 that is common to, or present in, both $d_3$ and $d_1$. In other words, the other region 645 is within the intersection of $d_3$ and $d_1$. Therefore, the second shift 632 may increase a captured region that originally included $d_1$ to further include a region $d_3$. Hence, when applying the particular window 612 to the second shifted plot 630, the computing component 111 may capture the stray signal 616, which was not captured when applying the particular window 612 to the plot 610. In summary, by applying both the first shift 622 and the second shift 632 to obtain the first shifted plot 620 and the second shifted plot 630, respectively, while subsequently capturing a region within the particular window 612 of the plot 610, the first shifted plot 620 and the second shifted plot 630, the computing component 111 superimposes the three aforementioned captured regions to obtain a region that includes $d_1$, $d_2$, and $d_3$, in other words, a union of $d_1$, $d_2$, and $d_3$, as illustrated in FIG. 6D.

Figure 6E:
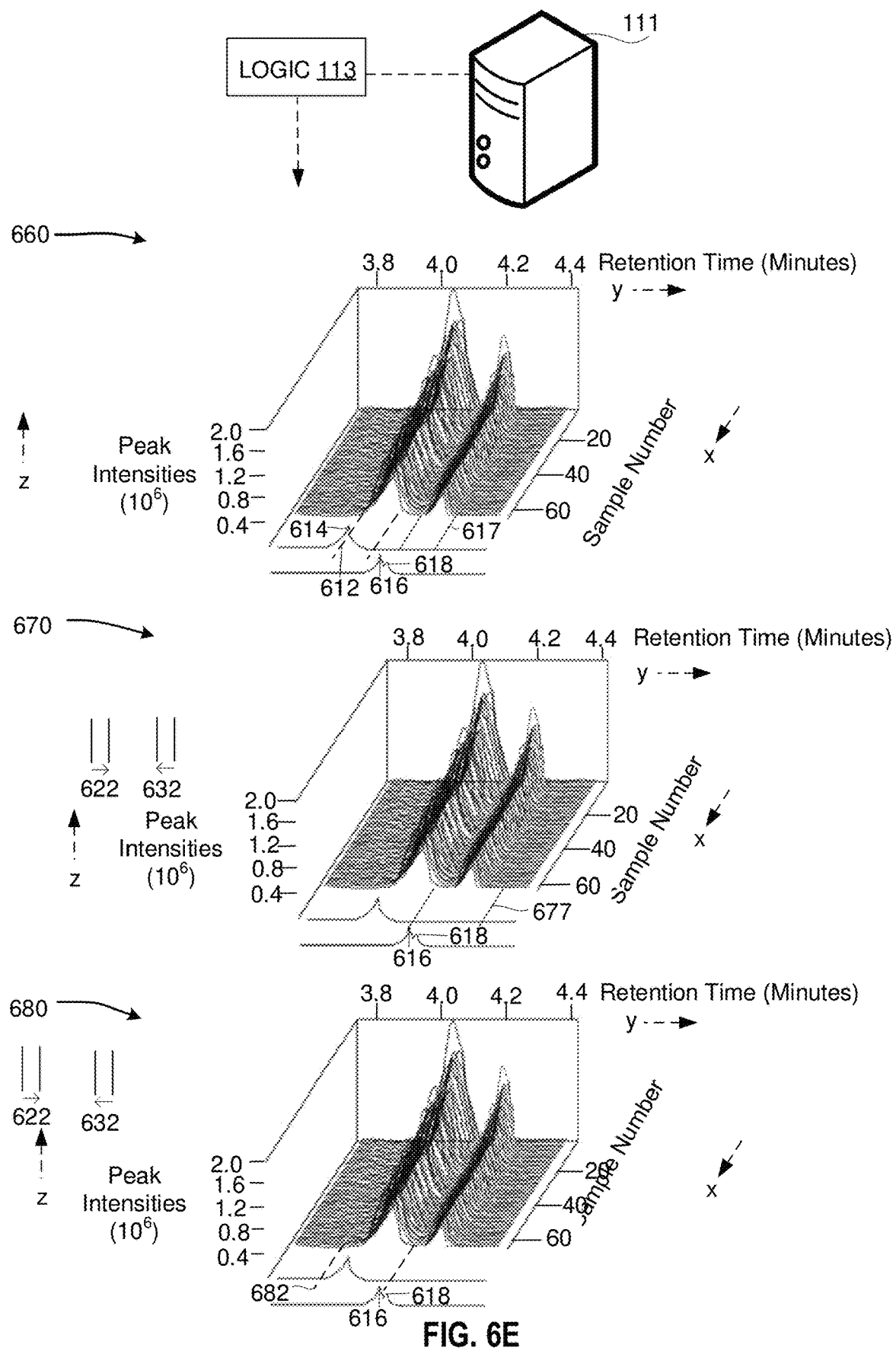

The above examples illustrated in FIGS. 6A-6D occur when no conflicts exist between neighboring windows. However, two neighboring windows that are sufficiently close together may be in conflict when both windows are expanded, and the resulting expanded windows at least partially coincide with each other. In such a scenario, the computing component 111 may determine only one of the two neighboring windows to expand based on which window has a higher signal intensity, such as a mean, median, mode, or highest signal intensity. An example of a conflict is illustrated in FIG. 6E, in which the particular window 612 conflicts with a second particular window 617. If the particular window 612 is expanded by the first shift 622 and the second particular window 617 is expanded by the second shift 632, at least respective portions of the resulting expanded windows may coincide. Because each window represents portions of different signals, one signal may not be included in two distinct windows. However, if the computing component 111 expanded both the particular window 612 and the second particular window 617, one signal may be erroneously included in both the resulting expanded windows. Thus, the computing component 111 may determine which one of the particular window 612 or the second particular window 617 to expand based on which of the particular window 612 or the second particular window 617 has a higher signal intensity. In FIG. 6E, the signal intensity within the particular window 612 is higher than that within the second particular window 617. Therefore, the computing component 111 may determine to expand the particular window 612 without expanding the second particular window 617.

In FIG. 6E, a plot 660 may include stray signals 616 and 618. A first shifted plot 670 illustrates that a stray signal 618 may be captured upon expansion of the second particular window 617 into an expanded window 677. To obtain the expanded window 677, the computing component 111 may apply same or similar principles as illustrated in FIGS. 6A-6D. Meanwhile, a second shifted plot 680 illustrates that the stray signal 616 may be captured upon expansion of the particular window 612 into an expanded window 682. To obtain the expanded window 682, the computing component 111 may apply same or similar principles as illustrated in FIGS. 6A-6D. Because signals within the particular window 612 have higher intensities compared to signals within the second particular window 617, the computing component 111 may expand the particular window 612 without expanding the second particular window 617, so that the stray signal 616 is captured but the stray signal 618 may not be captured. In such a manner, the computing component 111 resolves conflicts between two neighboring windows while capturing signals that are likely of higher intensities but disregarding signals that are likely of lower intensities. Therefore, the computing component 111 prioritizes higher intensity signals to preserve fidelity of such signals.

Figure 6F:
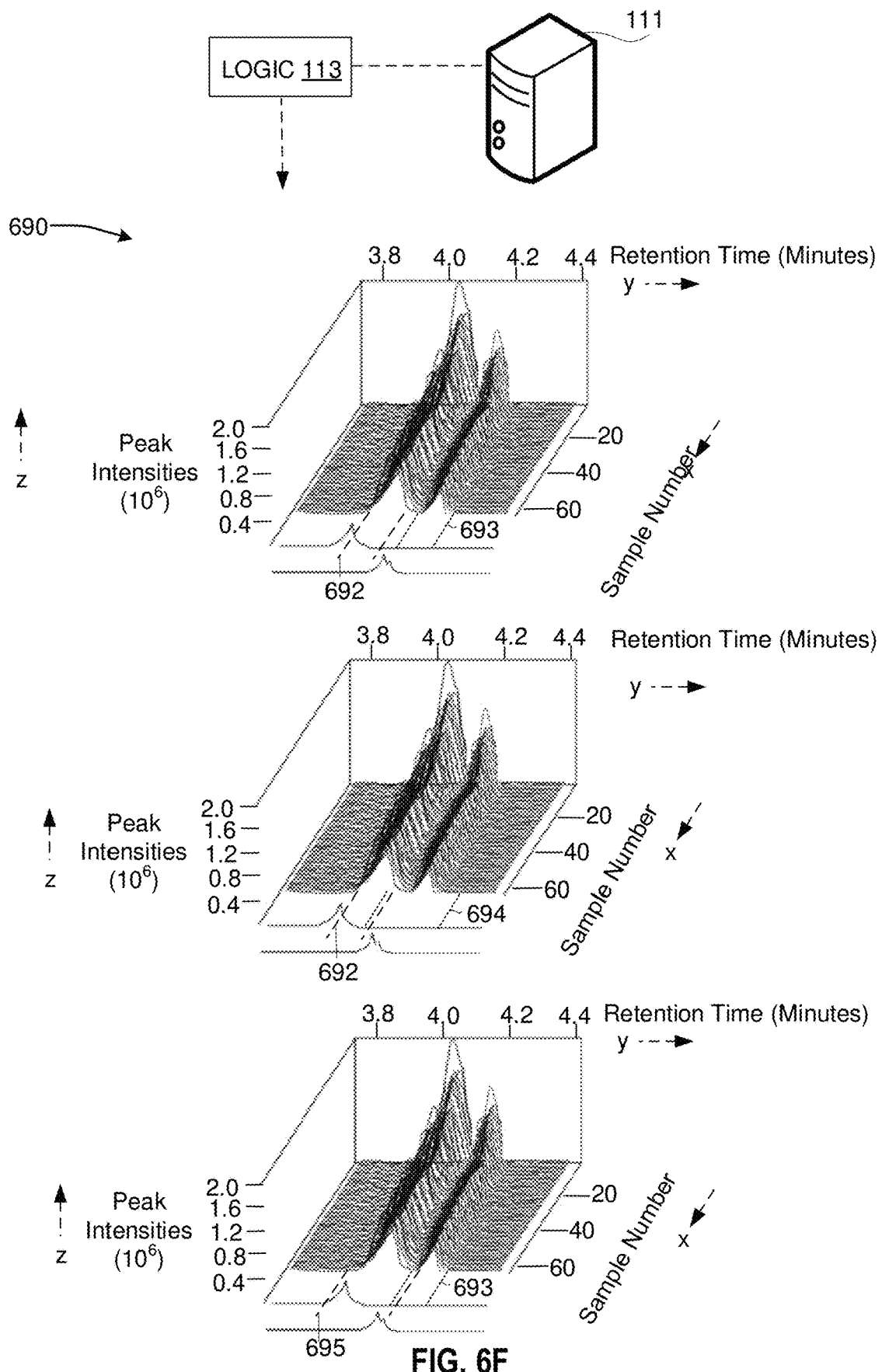

In other scenarios, if expansion of a first window coincides with a different, unexpanded window, then the computing component 111 may refrain from expanding the first window. For example, in FIG. 6F, the computing component 111 may determine or receive an indication of a first window 692 and a second window 693. As illustrated, if the second window 693 were expanded, then a resulting expanded window 694 would partially coincide with the first window 692. Likewise, if the first window 692 were expanded, then a resulting expanded window 695 would partially coincide with the second window 693. In such a scenario, the computing component 111 may refrain from expanding both the first window 692 and the second window 693.

Figure 7:
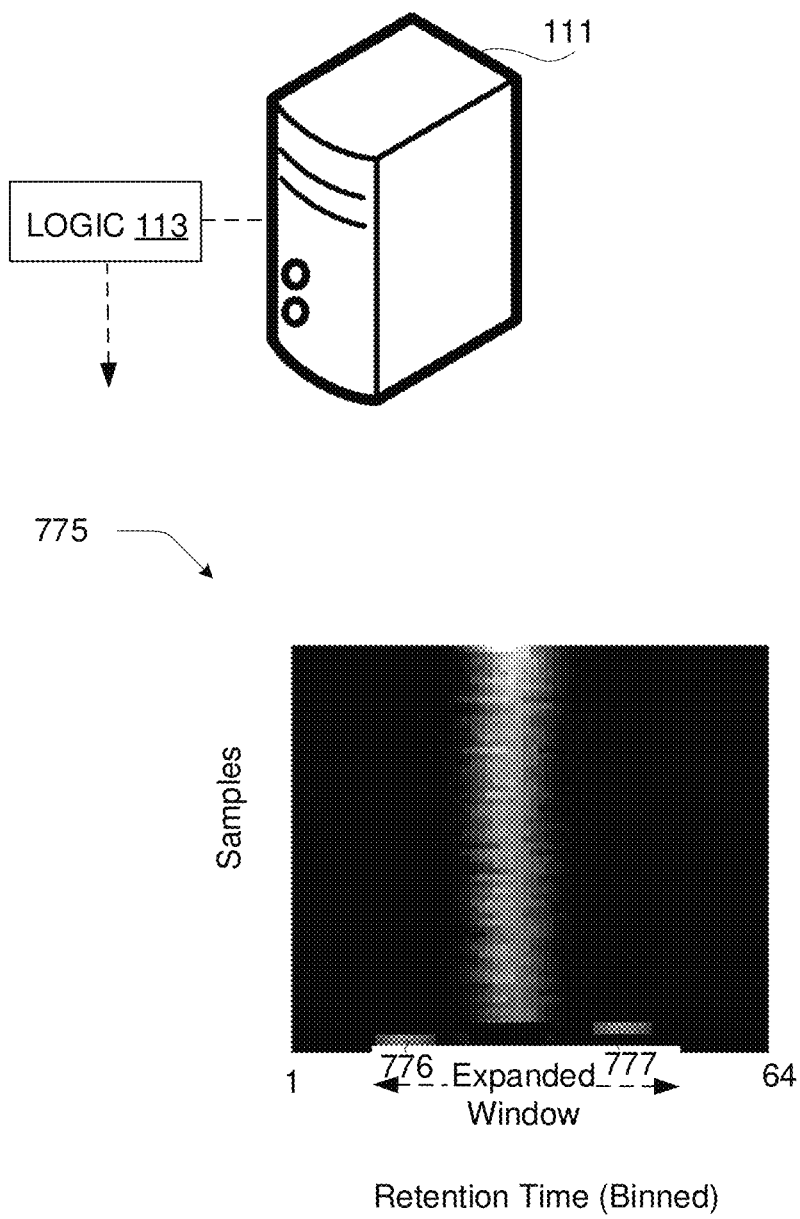
FIG. 7 is an exemplary illustration of a computing component that generates an updated input based on an expanded window for a machine learning model.

FIGS. 6A-6F illustrate a window expansion process with respect to the retention time axis. The window expansion process may expand an original window to redefine boundaries within which the computing component 111 may extract information. Referring back to FIG. 5F, the computing component 111 may generate an updated input, compared to the input 575, based on the expanded windows. An updated input 775 having an expanded window is illustrated in FIG. 7. The expanded window 775 may capture stray samples 776 and 777, which were outside of an original, unexpanded window. The computing component 111 may transmit the updated input that includes the expanded window 775 into the machine learning model, which may perform analysis or re-analysis. The computing component 111 may obtain occurrences and/or specific locations of maximum signal intensities within the expanded window. The computing component 111 may determine, within the expanded window, average retention times at which maximum intensities of particular signals occur across all samples to infer or predict the retention times corresponding to particular signals. Assume a simplified illustrative example having three samples, in which a first sample has a local maximum intensity corresponding to a particular signal occurring at 0.75 minutes, a second sample has a local maximum intensity corresponding to the particular signal occurring at 0.755 minutes, and a third sample has a local maximum intensity corresponding to the particular signal occurring at 0.76 minutes. Then, the computing component 111 would infer that the retention time corresponding to the particular signal occurs at 0.755 minutes.

As explained above, FIGS. 6A-6F and 7 illustrate the expansion of a retention time window. The computing component 111 may further perform an expansion of a window along the mass-to-charge ratio axis to obtain a range of mass-to-charge ratios and account for an error or tolerance. Such an expansion may be based on the obtained mass-to-charge ratio of the samples, for example, as determined with respect to FIG. 5E. For example, in FIG. 8, if an obtained mass-to-charge ratio 810 is 700.2375 and an error is 25 parts per million, a range 812 of the mass-to-charge ratios is between 700.219994 to 700.2550. Given a bin value of 0.025, the range of the mass-to-charge ratios may span three different mass-to-charge ratio bins, a first bin 814 from between 700.2 to 700.225, a second bin 816 from between 700.225 to 700.25 and a third bin 818 from between 700.25 to 700.275. The computing component 111 may extract information from the different mass-to-charge ratio bins 814, 816, and 818. However, if the obtained mass-to-charge ratio is within a proximity of a different mass-to-charge ratio, such that a difference between the obtained mass-to-charge ratio and the different mass-to-charge ratio does not exceed the error or tolerance, then the computing component 111 may not expand a window corresponding to the obtained mass-to-charge ratio, and the different mass-to-charge ratio, along the mass-to-charge ratio axis.

In such a manner, the computing component 111 leverages an image-based approach to process mass spectrometry data, to extract data that is most likely to represent a true signal within expanded windows while removing or reducing a number of noisy signals, or signals likely to be noise. Signals that are noisy or likely to be noise would probably occur in at most a small proportion of the data samples. Additionally, such an image-based approach further addresses shortcomings of existing signal, or wavelet-based approaches, which assume that mass spectrometry signals have particular shapes. Such an assumption may not always be valid, because mass spectrometry signals may not have Gaussian or symmetric shapes. Therefore, wavelet-based approaches may erroneously determine spurious signals as actual signals and fail to adequately remove noisy signals. In contrast, using an image-based approach, signals that fail to conform to Gaussian or symmetric, shapes may still be detected and not automatically erroneously determined to be noise or spurious.

Figure 9:
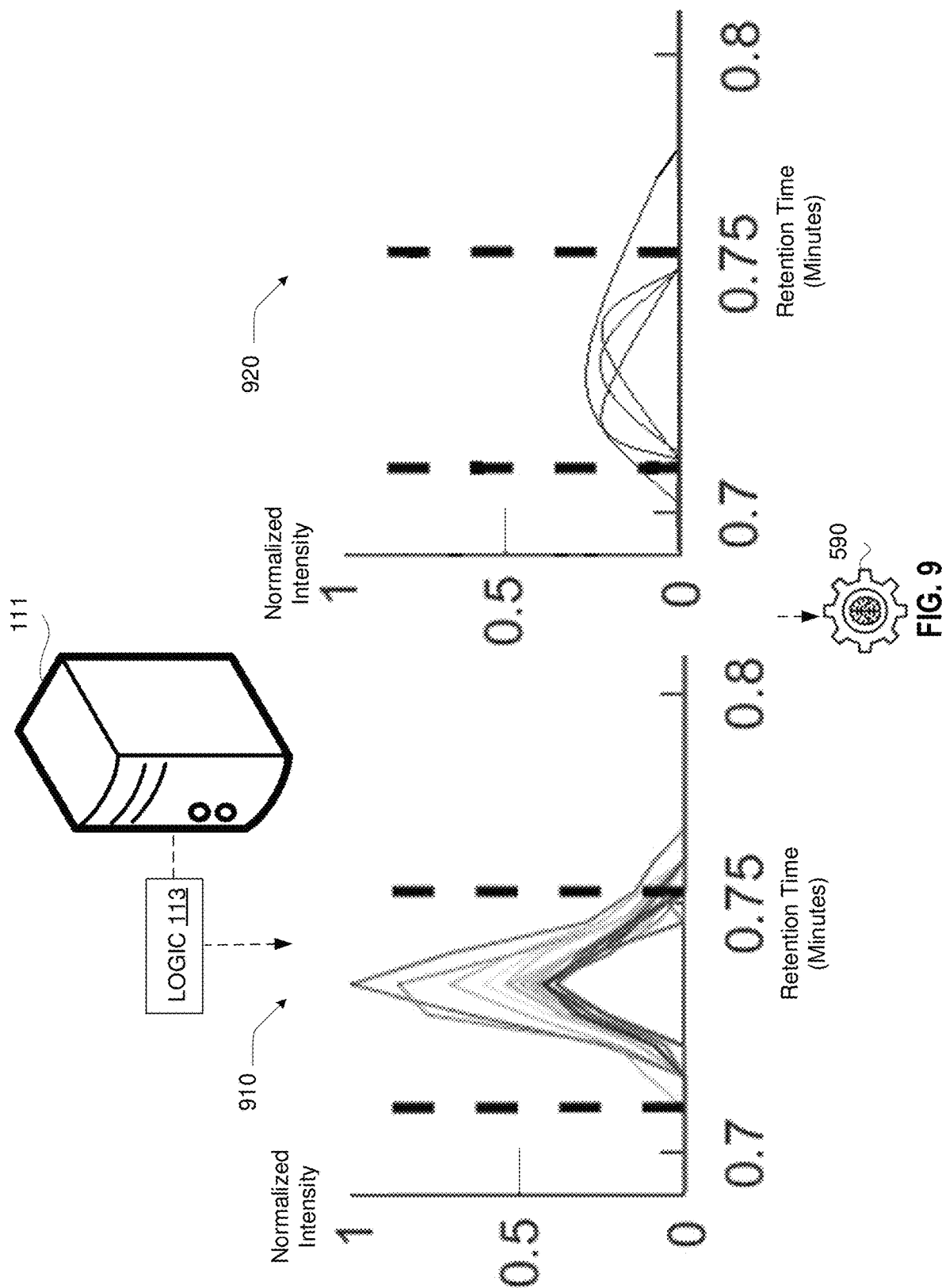
FIG. 9 is an exemplary illustration of a computing component that generates training data for a machine learning model.

The extracted data, with the expanded retention time windows and mass-to-charge ratio windows, may be fed, transmitted, or ingested into the machine learning model (e.g., the machine learning model 590), which determines or infers existence or absence, or veracity, of signals. As illustrated in FIG. 9, the machine learning model may require or receive at least a threshold number of true signals and/or at least a threshold number of spurious signals corresponding to each signal in order to determine or infer whether each signal is a true signal. The threshold number of true signals and/or spurious signals may be used to sequentially train the machine learning model. In some examples, a threshold number of true signals may be fed into the machine learning model. If a performance of the machine learning model is unsatisfactory, as determined, for example, by a loss coefficient, a threshold number of spurious signals may be fed into the machine learning model.

For example, the threshold number of true signals and/or spurious signals may be one hundred or fifty. As a specific illustrative scenario, if the machine learning model is determining or inferring an existence or absence of a signal at a retention time of 0.73 minutes and a mass-to-charge ratio of 700.025, the machine learning model may obtain a threshold number of true signals at that retention time and that mass-to-charge ratio, or within threshold ranges of that retention time and that mass-to-charge ratio. The threshold number of signals may include a first subset 910 of signals that are expected to be true signals, which may include signals of among highest intensities at that retention time and that mass-to-charge ratio. The threshold number of signals may also include a second subset 920 of signals that are expected to be false or spurious signals, or noise, at that retention time and that mass-to-charge ratio. In such a manner, the machine learning model may distinguish a true signal and a spurious signal at that particular retention time and mass-to-charge ratio. For each input (e.g., the input 775 with expanded mass-to-charge ratio windows), the machine learning model may output an indication or prediction of whether the signal within the expanded retention time window and the expanded mass-to-charge ratio window is true or spurious, and a confidence level or confidence interval of that determination or prediction.

From the output of the machine learning model, the computing component 111 may perform further quality control. The computing component 111 may retrieve retention times, mass-to-charge ratios, and other metrics or parameters including signal or peak counts across the samples in which each signal is present, corresponding to the signals indicated as true signals by the machine learning model. The computing component 111 may associate or correlate each of the signals indicated as true signals to a specific constituent, molecule, or compound (hereinafter "constituent") based on their respective mass-to-charge ratios and retention times, and determine whether the specific constituents match with predicted or expected constituents. The computing component 111 may determine a mass-to-charge ratio window and retention time window corresponding to each signal indicated as a true signal as described with respect to FIGS. 6A-6F and 7. The computing component 111 may retrieve one or more most frequently occurring signals within each mass-to-charge ratio window and retention time window, and correlate or associate the most frequently occurring signals with respective particular constituents. For example, if a set of samples in a specific experiment is predicted to have glutamate, aspartate, and butyric acid, the computing component 111 may determine whether any of the indicated true signals correlates to glutamate, aspartate, and butyric acid.

The computing component 111 may merge two signals, which have been indicated as true signals, that are both within an error or tolerance along the mass-to-charge ratio axis and within a threshold retention time of each other, then the two signals may be merged. The merging of the two signals may encompass extracting a higher intensity (e.g., median intensity) signal and/or disregarding a lower intensity signal. In some examples, the error or tolerance may be 10 parts per million, 20 parts per million, or 25 parts per million. In some examples, the threshold retention time may be 0.01 minutes. For example, if a first signal has a mass-to-charge ratio of 700.025, a retention time of 0.73 minutes, and an intensity of 1000, while a second signal has a mass-to-charge ratio of 700.035, a retention time of 0.735 minutes, and an intensity of 500, the computing component 111 may merge the first signal and the second signal by retaining the first signal and discarding or disregarding the second signal.

Figure 10:
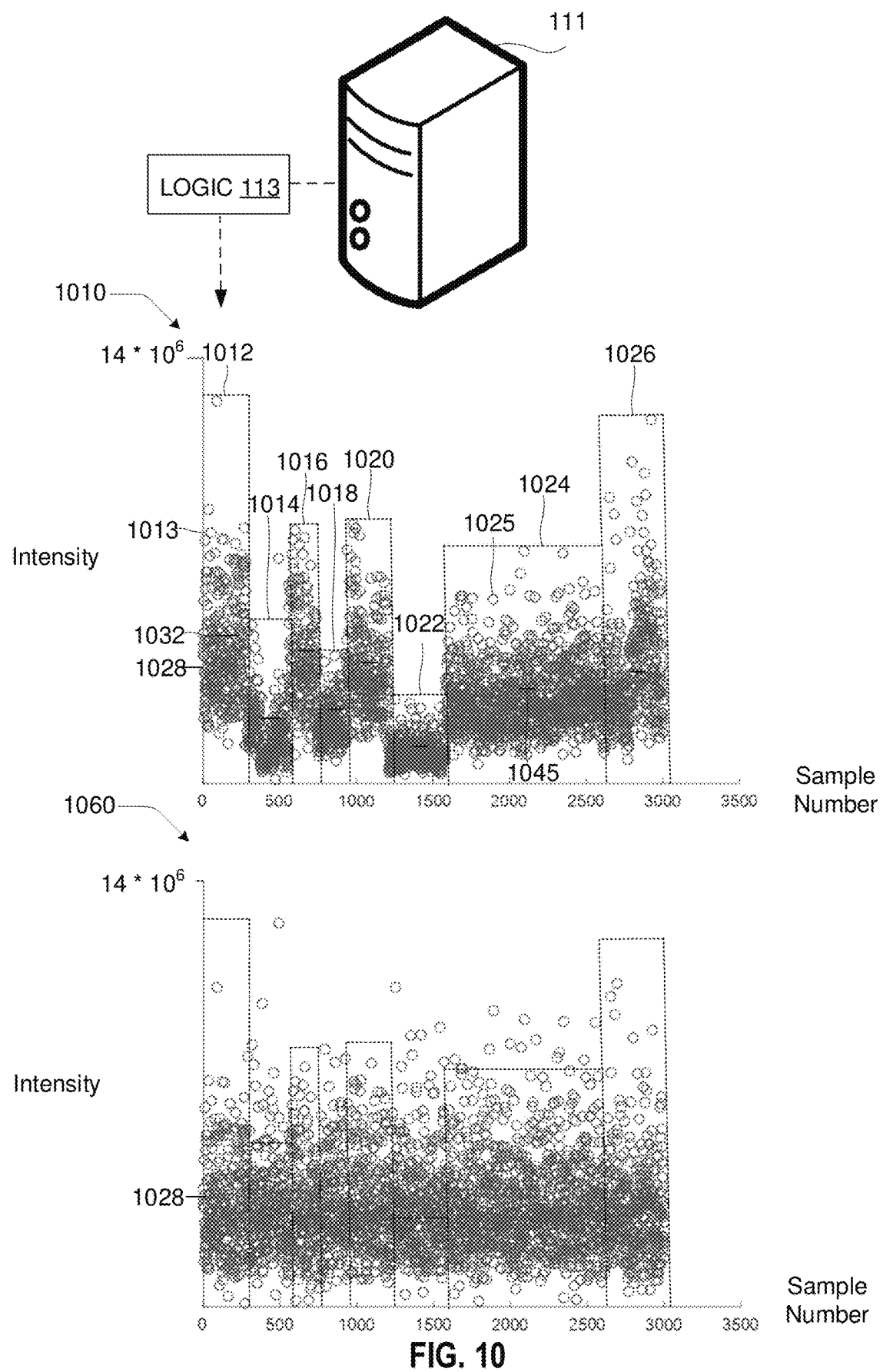
FIGS. 10-12 are exemplary illustrations of a computing component that performs adjustments or normalization of signal intensity across distinct batches or groups.

The computing component 111 may adjust or normalize (hereinafter "adjust") intensities to compensate for batch effects or other effects that cause inaccurate or nonuniform intensity readings. The adjusting may occur after merging. For example, the computing component 111 may detect batch effects when different groups or batches of common constituents exhibit a non-randomized distribution of intensities. The distinct batches may correspond to different times, settings, protocols, plates, or other instruments used to run the distinct batches. The computing component 111 may receive an indication of the different batches from experiment run information. As illustrated in FIG. 10, the computing component 111 may obtain or generate intensities 1010 of a particular constituent (e.g., glutamate) across all samples (e.g., 3050 samples) prior to adjusting of the intensities 1010. The computing component 111 may detect distinct batches 1012, 1014, 1016, 1018, 1020, 1022, 1024, and 1026. In each batch, a median intensity and/or distribution of intensities may have a statistically significant difference from median intensities and/or distributions of intensities in other batches. In some examples, a statistically significant p-value may be 0.01 or 0.001. The respective median intensities are illustrated as dashes within the respective batches 1012, 1014, 1016, 1018, 1020, 1022, 1024, and 1026 in FIG. 10. To adjust the intensities within each of the distinct batches 1012, 1014, 1016, 1018, 1020, 1022, 1024, and 1026, the computing component 111 may divide an intensity at each point, corresponding to a particular sample, by a median intensity specific to the batch to which the point belongs and multiply by a global median intensity 1028 across all samples (e.g., 3050 samples). For example, to adjust an intensity of a point 1013, the computing component 111 may divide the intensity of the point 1013 by a median intensity 932 of the batch 1012 and multiply by the global median intensity 1028. Therefore, all points within the batch 1012 are adjusted downward because the batch 1012 has a higher median intensity 1027 compared to the global median intensity 1027. To adjust an intensity of a point 1025 within the batch 1024, the computing component 111 may divide the intensity of the point 1025 by a median intensity 945 of the batch 1024 and multiply by the global median intensity 1028. More generally, the computing component 111 may obtain adjusted intensities as follows: $A=R*G/B$, wherein A denotes an adjusted intensity at a specific point, R denotes a non-adjusted intensity, G denotes a global median intensity (e.g., 1028) across all samples, and B denotes a batch median intensity (e.g., 1013, 1025). The computing component 111 may repeat this process for all points to obtain adjusted intensities 1060. Other methods of normalization may also be contemplated.

Figure 11:
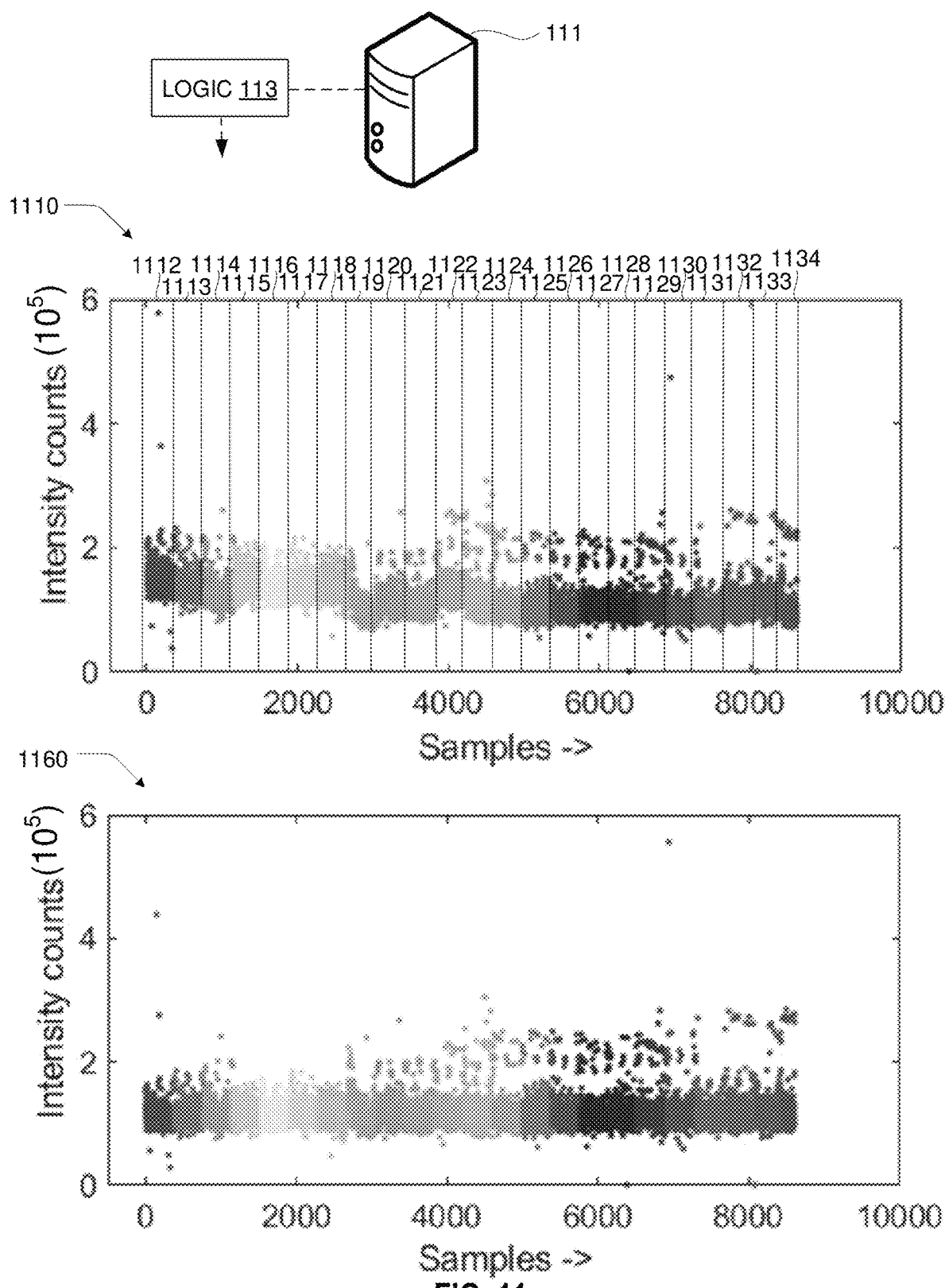
Figure 12:
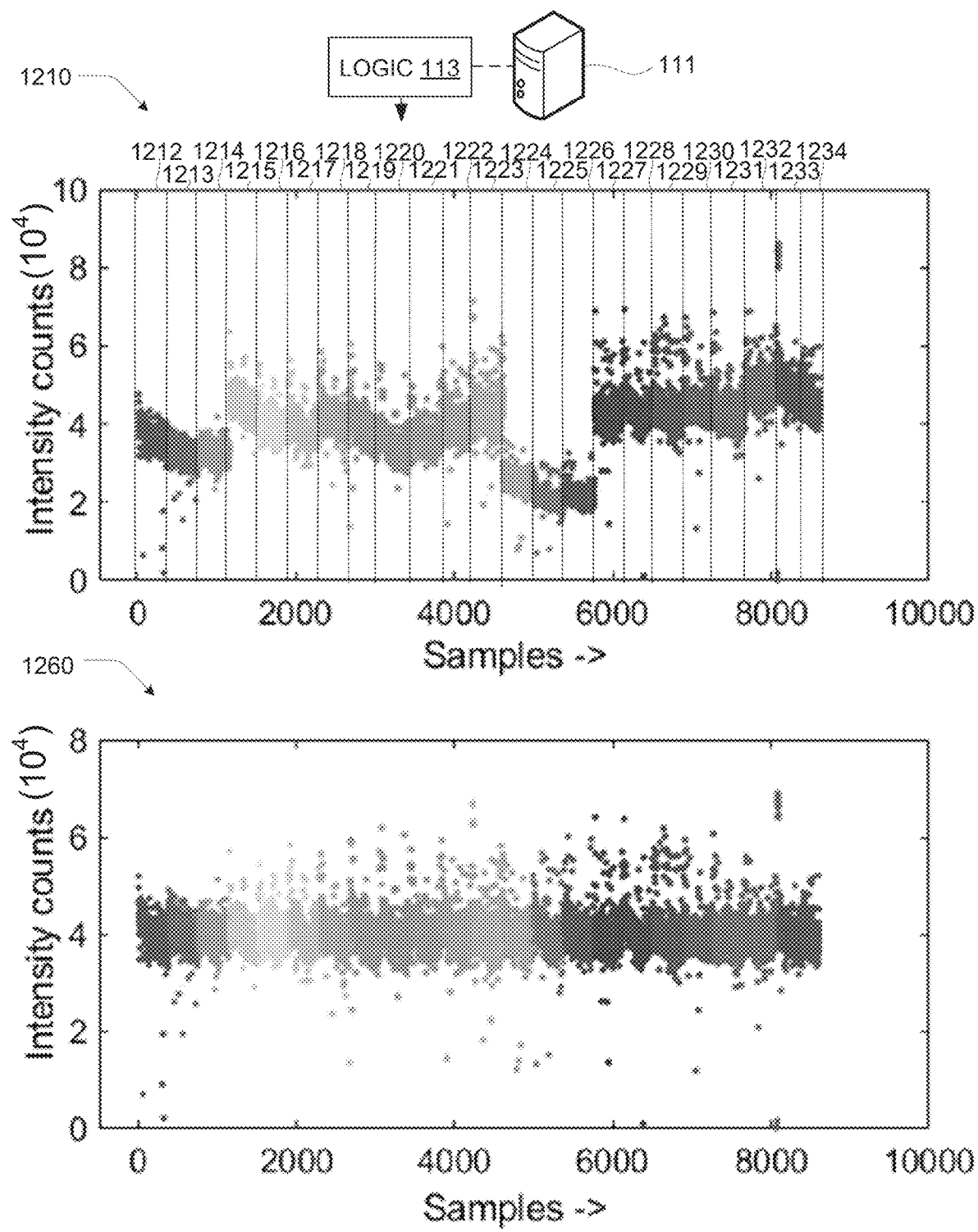

In FIG. 11, using same or similar principles of adjusting intensities across different batches as illustrated in FIG. 10, the computing component 111 may adjust intensities 1110 across batches 1112-1134 to obtain adjusted intensities 1160. In FIG. 12, using same or similar principles of adjusting intensities across different batches as illustrated in FIG. 9, the computing component 111 may adjust intensities 1110 across batches 1212-1234 to obtain adjusted intensities 1260.

In some examples, the computing component 111 may determine median intensity value corresponding to positively identified signals. For example, if the machine learning model positively indicates a presence of a signal at a retention time of 0.73 minutes and a mass-to-charge ratio of 700.025, the computing component 111 may determine the median intensity of the peak at that retention time and mass-to-charge ratio, following the quality control and adjusting procedures described above. If the median intensity is less than a specified threshold, the computing component 111 may refrain, or determine not to, further analyze the peak, but retain the information of such peaks. The information may be retained in the database 116.

The computing component 111 may further detect whether any signal intensities exhibit a non-random trend, such as, decreasing or increasing over time. For example, if any signal intensities of a particular constituent exhibit a decreasing or an increasing trend with respect to a run order (e.g., an order in which samples are injected into the liquid chromatograph mass spectrometer), the computing component 111 may attribute the decreasing or increasing intensities over time to inherent instabilities of particular constituents, rather than differences in original intensities or levels of the particular constituents in samples that were randomized before run. The computing component 111 may compare a rate of decrease or increase over time to a dissociation constant or other measure of degradation or instability of the particular constituent to determine or verify whether the decrease or increase over time is attributed to an inherent property of the particular constituent. For example, creatinine may degrade over time. Thus, even if an original level or concentration of creatinine in a particular sample was constant, samples that are run, injected, or inputted later may exhibit lower intensities of creatinine compared to samples that are run, injected, or inputted earlier. Additionally, some constituents may increase in level or concentration because those constituents may be formed due to degradation of other constituents.

Figure 13:
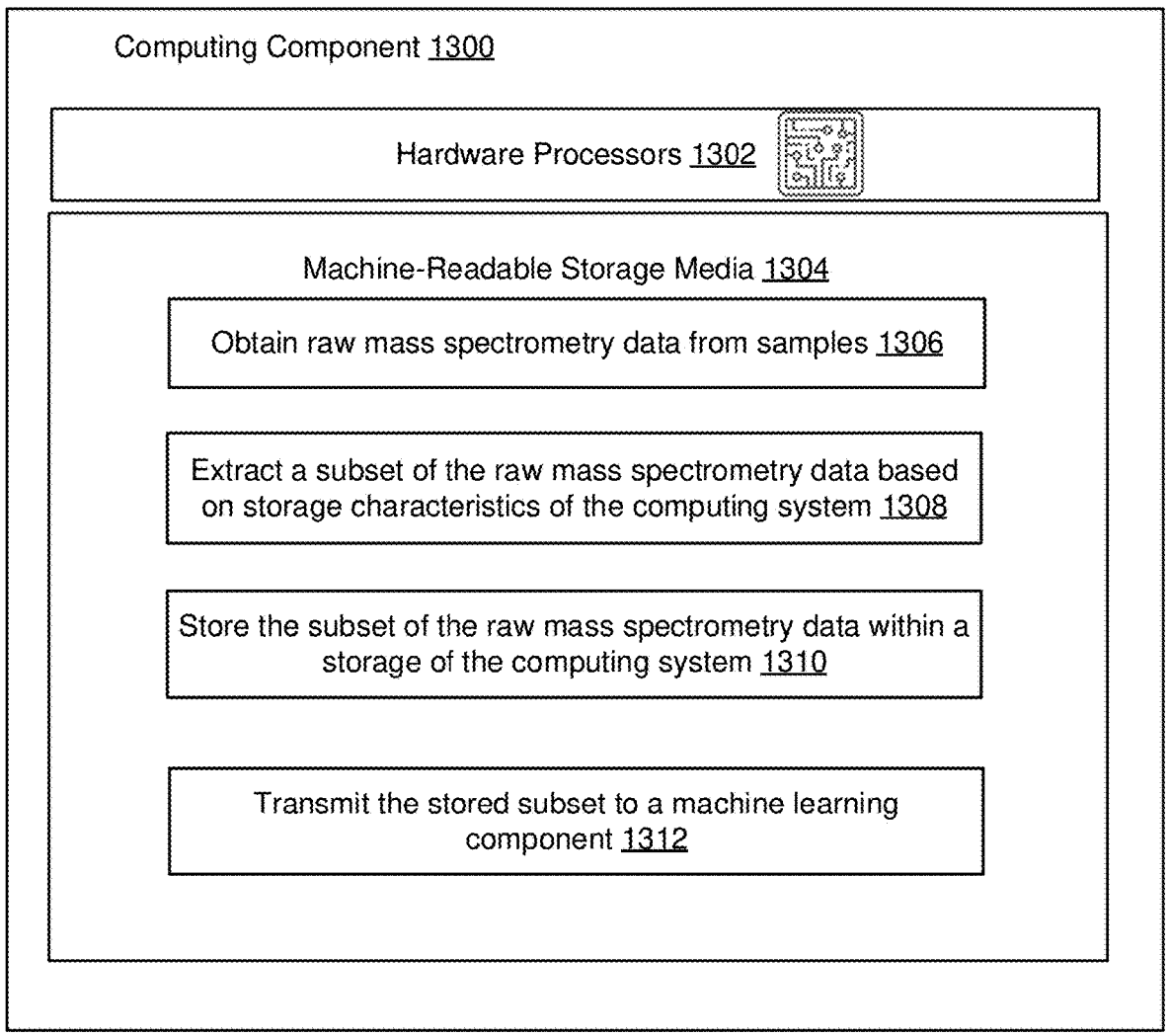
FIG. 13 is an exemplary flowchart, illustrating how a computing component eliminates or mitigates noisy mass spectrometry data, while also reducing computing costs of processing mass spectrometry data.

FIG. 13 illustrates a computing component 1300 that includes one or more hardware processors 1302 and machine-readable storage media 1304 storing a set of machine-readable/machine-executable instructions that, when executed, cause the hardware processor(s) 1302 to perform an illustrative method of efficiently processing and storing mass spectrometry data within storage confines of a computing system. It should be appreciated that there can be additional, fewer, or alternative steps performed in similar or alternative orders, or in parallel, within the scope of the various examples discussed herein unless otherwise stated. In some examples, steps or instructions (hereinafter "steps") 1306-1308 may serve as or form part of logic 113 of the computing component 111. The computing component 1300 may be implemented as the computing component 111 of FIGS. 1, 2, 3A-3E, 4A-4C, 5A-5F, 6A-6F, and 7-12. The machine-readable storage media 1304 may include suitable machine-readable storage media described in FIG. 14. FIG. 13 summarizes and further elaborates on some aspects previously described.

At step 1306, the hardware processor(s) 1302 may execute machine-readable/machine-executable instructions stored in the machine-readable storage media 1304 to obtain raw mass spectrometry data from samples. For example, the raw mass spectrometry data may include first data with respect to retention time in a first axis and second data with respect to a mass-to-charge ratio in a second axis, as illustrated in FIG. 1. The raw mass spectrometry data may be obtained over a threshold number of samples, such as thousands of samples, and in each sample, the raw mass spectrometry data may be in tabular format, with a first column indication retention times, a second column indicating mass-to-charge ratios, and a third column indicating signal intensities. The pictorial representation 120 has been illustrated in FIG. 1, in order to elucidate the particular information that may be encompassed within the raw mass spectrometry data. At step 1308, the hardware processor(s) 1302 may execute machine-readable/machine-executable instructions stored in the machine-readable storage media 1304 to extract or retrieve a subset of the raw mass spectrometry data based on storage characteristics, such as an available amount of storage capacity of the computing system. For example, the extracting or retrieving of the subset of the raw mass spectrometry data may include determining a number of passes of extracting or retrieving the subset of the raw mass spectrometry data. At step 1310, the hardware processor(s) 1302 may execute machine-readable/machine-executable instructions stored in the machine-readable storage media 1304 to store the subset of the raw mass spectrometry data within a storage (e.g., RAM) of the computing system. The storing of the subset may not be performed all at a single time instance, or in one pass, but rather, may be subdivided into multiple passes or batches, depending on an amount of computing storage space. Subdividing into multiple passes or batches may address the computing storage space being inadequate to store the entire subset. Thus, a first portion of the subset may be stored into the computing storage space in a first batch, then deleted, removed, or purged from the computing storage space after the first portion is transmitted to the machine learning component. Subsequently, a second portion of the subset may be stored into the computing storage space, then deleted, removed, or purged from the computing storage space after being transmitted to the machine learning component. At step 1312, the hardware processor(s) 1302 may execute machine-readable/machine-executable instructions stored in the machine-readable storage media 1304 to transmit the stored subset to a machine learning component.

Figure 14:
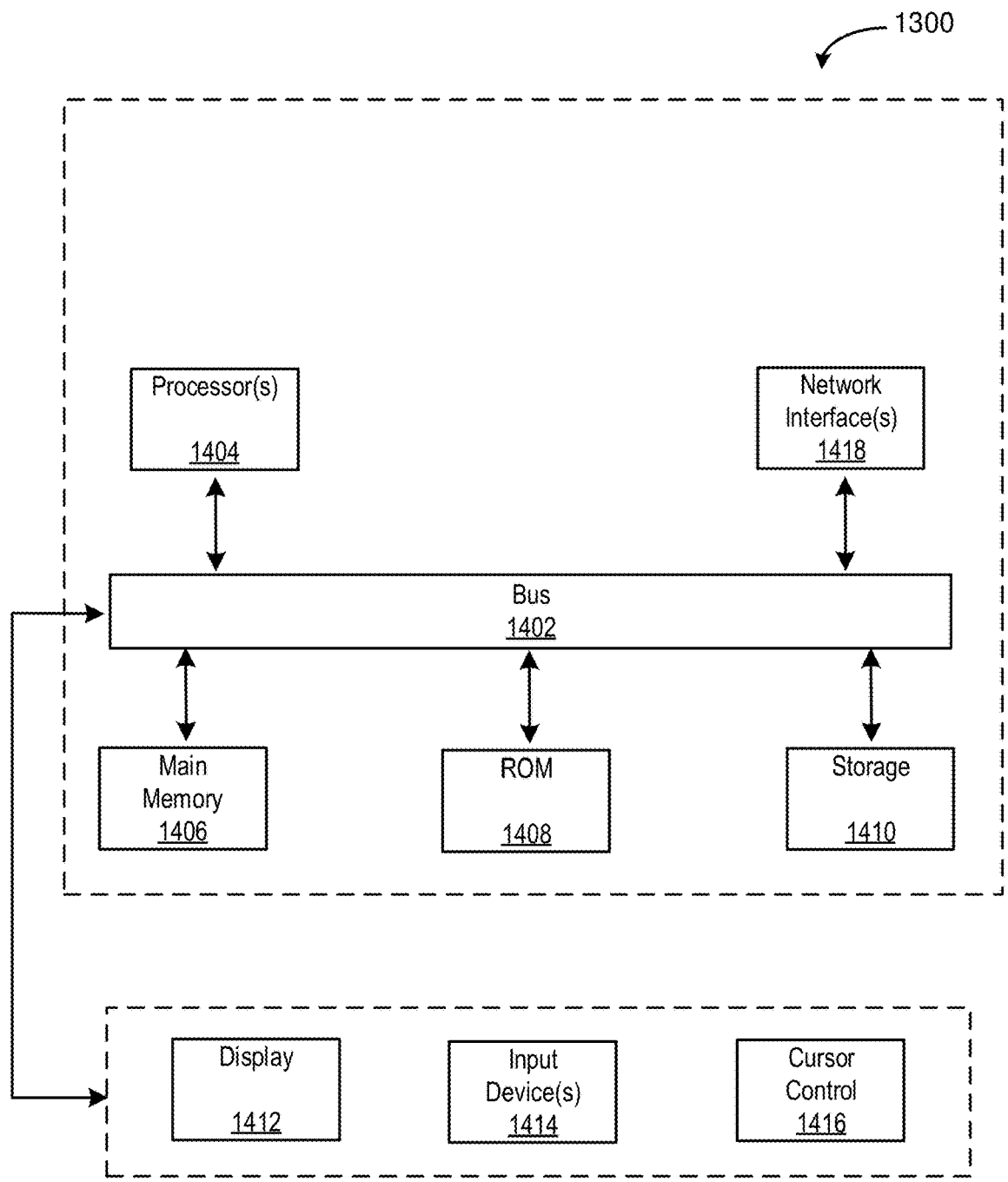
FIG. 14 is an example computing component that may be used to implement various features of examples described in the present disclosure.

FIG. 14 depicts a block diagram of an example computer system 1400 in which various of the examples described herein may be implemented. In some examples, the computer system 1400 may include a cloud-based or remote computing system. For example, the computer system 1400 may include a cluster of machines orchestrated as a parallel processing infrastructure. The computer system 1400 includes a bus 1402 or other communication mechanism for communicating information, one or more hardware processors 1404 coupled with bus 1402 for processing information. Hardware processor(s) 1404 may be, for example, one or more general purpose microprocessors. In some examples, the hardware processor(s) 1404 may implement the logic 113 of the computing component 111, as illustrated in any of FIGS. 1, 2, 3A-3E, 4A-4C, 5A-5F, 6A-6F, and 7-12.

The computer system 1400 also includes a main memory 1406, such as a random access memory (RAM), cache and/or other dynamic storage devices, coupled to bus 1402 for storing information and instructions to be executed by processor 1404. Main memory 1406 also may be used for storing temporary variables or other intermediate information during execution of instructions to be executed by the hardware processor(s) 1404. Such instructions, when stored in storage media accessible to the hardware processor(s) 1404, render computer system 1400 into a special-purpose machine that is customized to perform the operations specified in the instructions.

The computer system 1400 further includes a read only memory (ROM) 1408 or other static storage device coupled to bus 1402 for storing static information and instructions for the hardware processor(s) 1404. A storage device 1410, such as a magnetic disk, optical disk, or USB thumb drive (Flash drive), etc., is provided and coupled to bus 1402 for storing information and instructions.

The computer system 1400 may be coupled via bus 1402 to a display 1412, such as a liquid crystal display (LCD) (or touch screen), for displaying information to a computer user. An input device 1414, including alphanumeric and other keys, is coupled to bus 1402 for communicating information and command selections to the hardware processor(s) 1404. Another type of user input device is cursor control 1416, such as a mouse, a trackball, or cursor direction keys for communicating direction information and command selections to the hardware processor(s) 1404 and for controlling cursor movement on display 1412. In some examples, the same direction information and command selections as cursor control may be implemented via receiving touches on a touch screen without a cursor.

The computing system 1400 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "component," "system," "component," "database," "data store," and the like, as used herein, can refer to logic embodied in hardware or firmware, or to a collection of software instructions, possibly having entry and exit points, written in a programming language, such as, for example, Java, C or C++. A software component may be compiled and linked into an executable program, installed in a dynamic link library, or may be written in an interpreted programming language such as, for example, BASIC, Perl, or Python. It will be appreciated that software components may be callable from other components or from themselves, and/or may be invoked in response to detected events or interrupts. Software components configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware components may be comprised of connected logic units, such as gates and flip-flops, and/or may be comprised of programmable units, such as programmable gate arrays or processors.

The computer system 1400 may implement the techniques described herein using customized hard-wired logic, one or more ASICs or FPGAs, firmware and/or program logic which in combination with the computer system causes or programs computer system 1400 to be a special-purpose machine. According to one example, the techniques herein are performed by computer system 1400 in response to the hardware processor(s) 1404 executing one or more sequences of one or more instructions contained in main memory 1406. Such instructions may be read into main memory 1406 from another storage medium, such as storage device 1410. Execution of the sequences of instructions contained in main memory 1406 causes the hardware processor(s) 1404 to perform the process steps described herein. In alternative examples, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 1410. Volatile media includes dynamic memory, such as main memory 1406. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 1402. Transmission media can also take the form of acoustic or light waves, such as those generated during radio-wave and infra-red data communications.

The computer system 1400 also includes a communication interface 1418 coupled to bus 1402. Network interface 1418 provides a two-way data communication coupling to one or more network links that are connected to one or more local networks. For example, communication interface 1418 may be an integrated services digital network (ISDN) card, cable modem, satellite modem, or a modem to provide a data communication connection to a corresponding type of telephone line. As another example, network interface 1418 may be a local area network (LAN) card to provide a data communication connection to a compatible LAN (or WAN component to communicated with a WAN). Wireless links may also be implemented. In any such implementation, network interface 1418 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world wide packet data communication network now commonly referred to as the "Internet." Local network and Internet both use electrical, electromagnetic or optical signals that carry digital data streams. The signals through the various networks and the signals on network link and through communication interface 1418, which carry the digital data to and from computer system 1400, are example forms of transmission media.

The computer system 1400 can send messages and receive data, including program code, through the network(s), network link and communication interface 1418. In the Internet example, a server might transmit a requested code for an application program through the Internet, the ISP, the local network and the communication interface 1418.

The received code may be executed by the hardware processor(s) 1404 as it is received, and/or stored in storage device 1410, or other non-volatile storage for later execution.

Each of the processes, methods, and algorithms described in the preceding sections may be embodied in, and fully or partially automated by, code components executed by one or more computer systems or computer processors comprising computer hardware. The one or more computer systems or computer processors may also operate to support performance of the relevant operations in a "cloud computing" environment or as a "software as a service" (SaaS). The processes and algorithms may be implemented partially or wholly in application-specific circuitry. The various features and processes described above may be used independently of one another, or may be combined in various ways. Different combinations and sub-combinations are intended to fall within the scope of this disclosure, and certain method or process blocks may be omitted in some implementations. The methods and processes described herein are also not limited to any particular sequence, and the blocks or states relating thereto can be performed in other sequences that are appropriate, or may be performed in parallel, or in some other manner. Blocks or states may be added to or removed from the disclosed example examples. The performance of certain of the operations or processes may be distributed among computer systems or computers processors, not only residing within a single machine, but deployed across a number of machines.

As used herein, a circuit might be implemented utilizing any form of hardware, software, or a combination thereof. For example, one or more processors, controllers, ASICs, PLAs, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. Even though various features or elements of functionality may be individually described or claimed as separate circuits, these features and functionality can be shared among one or more common circuits, and such description shall not require or imply that separate circuits are required to implement such features or functionality. Where a circuit is implemented in whole or in part using software, such software can be implemented to operate with a computing or processing system capable of carrying out the functionality described with respect thereto, such as computer system 1400.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain examples include, while other examples do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

Unless the context requires otherwise, throughout the present specification and claims, the word "comprise" and variations thereof, such as, "comprises" and "comprising" are to be construed in an open, inclusive sense, that is as "including, but not limited to." Recitation of numeric ranges of values throughout the specification is intended to serve as a shorthand notation of referring individually to each separate value falling within the range inclusive of the values defining the range, and each separate value is incorporated in the specification as it were individually recited herein. Additionally, the singular forms "a," "an" and "the" include plural referents unless the context clearly dictates otherwise. The phrases "at least one of," "at least one selected from the group of," or "at least one selected from the group consisting of," and the like are to be interpreted in the disjunctive (e.g., not to be interpreted as at least one of A and at least one of B).

What is claimed is:

1. A computer-implemented method performed by a computing system, comprising:
    obtaining raw mass spectrometry data from samples;
    transforming the raw mass spectrometry data into a binned representation by binning the raw mass spectrometry data, wherein the binned representation comprises local peak signals in each bin;
    transforming the binned representation into a frequency representation, wherein the frequency representation comprises a three-dimensional (3-D) representation and is indicative of frequencies of occurrence of the local peak signals across the samples, wherein the transforming of the binned representation comprises:
        removing a subset of the local peak signals based on the frequencies of occurrence across the samples and retaining a remaining subset of the local peak signals; and
        segmenting the remaining subset of the local peak signals, wherein the segmenting comprises:
            inverting each of the remaining subset of the local peak signals and determining separate rising or falling edges of each of the remaining subset or determining demarcations between the separate rising and falling edges, wherein the inverting distinguishes between two separate local peak signals;
    determining windows around each of the segmented remaining subset of the local peak signals;
    generating a windowed plot that captures each of the segmented remaining subset of the local peak signals according to the determined windows;
    expanding the windows by obtaining offset plots that are offset from each of the windowed plots, wherein each of the offset plots comprises an additional local peak signal that is absent from a corresponding windowed plot;
    overlaying the offset plots over the corresponding windowed plots to create overlaid windowed plots;
    extracting a subset of the segmented remaining subset of the local peak signals within the overlaid windowed plots based on storage characteristics of the computing system;
    storing the subset of the segmented remaining subset of the local peak signals within a storage of the computing system;

inputting the overlaid windowed plots to a machine learning component;
obtaining, from the machine learning model, veracities or predicted veracities of each of the segmented remaining subset of the local peak signals;
based on the obtained veracities, outputting one or more constituents of the samples; and
performing a medical treatment based on the one or more constituents, wherein the medical treatment comprises restoring a level of the one or more constituents to a normal level.

2. The computer-implemented method of claim 1, wherein the raw mass spectrometry data comprises a full list of candidate signals, and the storing of the segmented remaining subset of the local peak signals comprises:
determining an available amount of space within the storage;
reserving a second amount of space, the second amount of space being a portion or all of the available amount of space; and
determining a number of batches to extract the subset based on the reserved second amount of space, wherein the extracting of the subset comprises subdividing the segmented remaining subset of the local peak signals into the determined number of batches.

3. The computer-implemented method of claim 2, wherein the determining of a number of batches comprises:
determining a corresponding number of the segmented remaining subset of the local peak signals that when stored, consumes the reserved second amount of space; and
determining or estimating a corresponding mass-to-charge ratio interval from which the determined number of the segmented remaining subset of the local peak signals is extracted, wherein:
the determined number of batches is based on a quotient between an entire mass-to-charge ratio interval and the determined or estimated mass-to-charge ratio interval, and
in each batch, a portion of the segmented remaining subset of the local peak signals is extracted from an interval having a size of the determined or estimated mass-to-charge ratio interval.

4. The computer-implemented method of claim 3, further comprising:
determining a bin value to apply to the mass spectrometry data; and
in response to determining or estimating a corresponding mass-to-charge ratio interval, determining a number of bins corresponding to the determined or estimated mass-to-charge ratio interval, wherein in each batch, the portion of the segmented remaining subset of the local peak signals is extracted from the determined number of bins.

5. The computer-implemented method of claim 1, wherein the retaining a remaining subset of the local peak signals is based on highest intensities of the local peak signals.

6. The computer-implemented method of claim 1, wherein:
the extracting of the subset of the segmented remaining subset of the local peak signals comprises extracting individual signals,
each individual signal having a length or a number of pixels between 100 and 1000, inclusive, and consumes four bytes of storage space per unit length or pixel.

7. A computing system comprising:
one or more processors; and
a memory storing instructions that, when executed by the one or more processors, cause the one or more processors to:
obtain raw mass spectrometry data from samples;
transform the raw mass spectrometry data into a binned representation by binning the raw mass spectrometry data, wherein the binned representation comprises local peak signals in each bin;
transform the binned representation into a frequency representation, wherein the frequency representation comprises a three-dimensional (3-D) representation and is indicative of frequencies of occurrence of the local peak signals across the samples, wherein the transforming of the binned representation comprises:
removing a subset of the local peak signals based on the frequencies of occurrence across the samples and retaining a remaining subset of the local peak signals; and
segmenting the remaining subset of the local peak signals, wherein the segmenting comprises:
inverting each of the remaining subset of the local peak signals and determining separate rising or falling edges of each of the remaining subset or determining demarcations between the separate rising and falling edges, wherein the inverting distinguishes between two separate local peak signals;
determine windows around each of the segmented remaining subset of the local peak signals;
generate a windowed plot that captures each of the segmented remaining subset of the local peak signals according to the determined windows;
expand the windows by obtaining offset plots that are offset from each of the windowed plots, wherein each of the offset plots comprises an additional local peak signal that is absent from a corresponding windowed plot;
overlay the offset plots over the corresponding windowed plots to create overlaid windowed plots;
extract a subset of the segmented remaining subset of the local peak signals within the overlaid windowed plots based on storage characteristics of the computing system;
store the subset of the segmented remaining subset of the local peak signals within a storage of the computing system;
input the overlaid windowed plots to a machine learning component;
obtain, from the machine learning model, veracities or predicted veracities of each of the segmented remaining subset of the local peak signals;
based on the obtained veracities, output one or more constituents of the samples; and
perform a medical treatment based on the one or more constituents, wherein the medical treatment comprises restoring a level of the one or more constituents to a normal level.

8. The computing system of claim 7, wherein the raw mass spectrometry data comprises a full list of candidate signals, and the storing of the segmented remaining subset of the local peak signals comprises:
determining an available amount of space within the storage;

reserving a second amount of space, the second amount of space being a portion or all of the available amount of space; and determining a number of batches to extract the subset based on the reserved second amount of space, wherein the extracting of the subset comprises subdividing the segmented remaining subset of the local peak signals into the determined number of batches.

9. The computing system of claim 8, wherein the determining of a number of batches comprises:

determining a corresponding number of the segmented remaining subset of the local peak signals that when stored, consumes the reserved second amount of space; and determining or estimating a corresponding mass-to-charge ratio interval from which the determined number of the segmented remaining subset of the local peak signals is extracted, wherein:

the determined number of batches is based on a quotient between an entire mass-to-charge ratio interval and the determined or estimated mass-to-charge ratio interval, and in each batch, a portion of the segmented remaining subset of the local peak signals is extracted from an interval having a size of the determined or estimated mass-to-charge ratio interval.

10. The computing system of claim 9, wherein the instructions further cause the one or more processors to:

determine a bin value to apply to the mass spectrometry data; and in response to determining or estimating a corresponding mass-to-charge ratio interval, determining a number of bins corresponding to the determined or estimated mass-to-charge ratio interval, wherein in each batch, the portion of the segmented remaining subset of the local peak signals is extracted from the determined number of bins.

11. The computing system of claim 7, wherein the retaining a remaining subset of the local peak signals is based on highest intensities of the local peak signals.

12. The computing system of claim 7, wherein:

the extracting of the subset of the segmented remaining subset of the local peak signals comprises extracting individual signals, each individual signal having a length or a number of pixels between 100 and 1000, inclusive, and consumes four bytes of storage space per unit length or pixel.

* * * * *